US005602147A

United States Patent [19]
Carr et al.

[11] Patent Number: 5,602,147
[45] Date of Patent: Feb. 11, 1997

[54] PIPERIDINYL THIACYCLIC DERIVATIVES

[75] Inventors: Albert A. Carr; John M. Kane; George D. Maynard; Hsien C. Cheng, all of Cincinnati; Mark W. Dudley, Somerville, all of Ohio

[73] Assignee: Merrell Pharmaceuticals Inc., Cincinnati, Ohio

[21] Appl. No.: 456,590

[22] Filed: Jun. 1, 1995

Related U.S. Application Data

[62] Division of Ser. No. 281,943, Jul. 28, 1994, Pat. No. 5,476,861, which is a division of Ser. No. 201,149, Feb. 24, 1994, Pat. No. 5,371,093, which is a continuation of Ser. No. 76,268, Jun. 11, 1993, abandoned, which is a continuation of Ser. No. 835,658, Feb. 13, 1992, abandoned.

[51] Int. Cl.$^6$ ............... A61K 31/445; C07D 417/02
[52] U.S. Cl. .............. 514/321; 514/324; 546/209; 546/212
[58] Field of Search ............... 586/209, 212; 574/321, 324

[56] References Cited

U.S. PATENT DOCUMENTS

| | | | |
|---|---|---|---|
| 2,739,968 | 3/1956 | Sperber | 546/212 |
| 2,838,516 | 6/1958 | Hoffman et al. | 546/212 |
| 3,122,561 | 2/1964 | Cason | 546/212 |
| 3,806,526 | 4/1974 | Carr | 546/212 |
| 3,835,131 | 9/1974 | Strehlke | 546/209 |
| 3,878,217 | 4/1975 | Carr et al. | 546/213 |
| 4,168,315 | 9/1979 | Rynbramdt | 546/209 |
| 4,219,559 | 8/1980 | Janssen et al. | 546/199 |
| 4,254,129 | 3/1981 | Carr et al. | 546/239 |
| 4,283,405 | 8/1981 | Engel et al. | 546/213 |
| 4,285,957 | 8/1981 | Carr et al. | 546/239 |
| 4,310,465 | 1/1982 | Olson et al. | 552/310 |
| 4,559,349 | 12/1985 | Storni | 514/318 |
| 4,680,296 | 7/1987 | Manoury et al. | 514/259 |
| 4,695,575 | 9/1987 | Janssens et al. | 514/322 |
| 4,810,713 | 3/1989 | Yanni | 514/317 |
| 4,879,301 | 11/1989 | Umio et al. | 514/321 |
| 4,908,372 | 3/1990 | Carr et al. | 514/322 |
| 4,950,674 | 8/1990 | Yanni et al. | 514/317 |
| 5,006,536 | 4/1991 | Effland | 514/321 |
| 5,032,598 | 7/1991 | Baldwin et al. | 514/318 |
| 5,064,840 | 11/1991 | Carr et al. | 514/322 |
| 5,070,087 | 12/1991 | Teng | 514/212 |
| 5,380,731 | 1/1995 | Carr et al. | 514/322 |
| 5,385,916 | 1/1995 | Howard | 514/321 |
| 5,432,175 | 7/1995 | Piwinski | 514/252 |

FOREIGN PATENT DOCUMENTS

| | | |
|---|---|---|
| 2029275 | 5/1991 | Canada . |
| 0013612 | 1/1980 | European Pat. Off. . |
| 0037265 | 10/1981 | European Pat. Off. . |
| 0151826 | 8/1985 | European Pat. Off. . |
| 0331511 | 9/1989 | European Pat. Off. . |
| 0351194 | 1/1990 | European Pat. Off. . |
| 0377457 | 7/1990 | European Pat. Off. . |
| 0381375 | 8/1990 | European Pat. Off. . |
| 54145673 | 11/1979 | Japan . |
| 6045639 | 10/1985 | Japan . |
| 63-93779 | 4/1988 | Japan . |
| 10052776 | 2/1989 | Japan . |
| 1227987 | 10/1991 | Japan . |
| 93/20063 | 10/1993 | WIPO . |

OTHER PUBLICATIONS

Lipshutz et al, "More Highly Mixed, higher order cyanocuprates . . . ", Journal of Organometallic Chemistry, 285 (1985) pp. 437–447.

Molloy et al, 433908, "Organdtin Biocides . . . ", Index Chemicus vol. 114, Issue 1340, 1989.

Donidoni et al, "A concise thiazole mediated synthesis of . . . ", Tetrahedron Vo., 45, No. 16, pp. 5141 to 5150, 1989.

Xiaoming et al, "Room temperature stable 3–Lithiothiophene; a facile synthesis of 3–functional thiophenes" Tetrahedron Letters, vol. 35, No. 22 pp. 3673–3674, 1994.

Rohloff et al, "Eantioselective sysnthesis of 5–LO Inhibitors using a Gulofuranose auxiliary", Tetrahedron Letters, vol. 35, No. 7, pp. 1011–1014, 1994.

McOmie, "Protective Groups in Organic Chemistry", Plenum Press, (1973), p. 49.

Honkanen, Erkki et al, J. Med. Chem., 26(10), 1433–1438, 1983.

Chemical Abstracts, 51:12151f (1956).

Maynard et al, "A Convergent synthesis of 4–2–benzothiazoyl) Piperidines with antihistaminic activity" Bioorg. Med. Chem. Litt. v. 3, pp. 753–756 (1993).

X copies in copending SN 08/457.929.

Ohta et al., Synthesis and Application of Imidazole Derivatives. Synthesis and Acyl Activation of 2–Acyl–1–methyl–1H–imidazoles, Chem. Pharm. Bull. 34(12) pp. 4916–4926 (1986).

Katritzky, Ed., Comprehensive Heterocyclic Chemistry, Part 4A, Pergamon Press 1984.

Katritzky et al., Synthesis of 2–Substituted Imidazoles and Benzimidazoles and of 3–Substituted Pyrazoles by Lithiation of N–(Dialkylamino)methyl Heterocycles, J. Org. Chem. 53 pp. 5685–5689 (1988).

Chadwick et al., 2,5–Dilithiation of N–Protected Imidazoles. Syntheses of 2,5–Disubstituted Derivatives of 1–Methoxymethyl–, 1–Triphenylmethyl–, and 1–(N, N–Dimethylsulphonamido)–imidazole, Chem. Soc. Perkin Trans. 1, pp. 481–486 (1984).

Manoharan et al., 1–(1–Ethoxyethyl): An Effective Protecting Group for Imidazole Nitrogen, J. Org. Chem. 53 pp. 1107–1110 (1988).

Carr et al., J. of Org. Chem., 1990, vol. 55, pp. 1399–1401.

Barnett et al., New Perspectives in Histamine Research, Birhauser Verlag Basel 1991, pp. 181–196.

Glennon, Journal of Medicinal Chemistry, vol. 30, No. 1, Jan., 1987, pp. 1–12.

(List continued on next page.)

Primary Examiner—Ceila Chang
Attorney, Agent, or Firm—William R. Boudreaux

[57] ABSTRACT

Piperidinyl thiacyclic derivatives useful in the treatment of allergic diseases and diseases responding to antagonism of 5HT$_2$ receptors, pharmaceutical compositions and a methods of treatment using these compounds.

9 Claims, No Drawings

OTHER PUBLICATIONS

Kokohmskaya et al., Chemical Abstract, vol. 102, p. 615 Abstract No. 131879r. (1985).

"Organic Chemistry" Morrison and Boyd, pp. 630, 715, 746, Allyn and Bacon, Inc. 3rd Edition (1976).

"Synthetic Organic Chemistry" Wagner and Zook, p. 675 John Wiley & Sons, Inc. 1953.

Glennon, Journal of Medicinal Chemistry, vol. 30, No. 1, Jan., 1987, pp. 1–12.

Remington's Pharmaceutical Sciences, 16th Edition, pp. 1066–1067 (Mack Publishing Co., 1980).

*Chemical Abstracts,* vol. 92, No. 23, 9 Jun. 1980, abstract No. 198261b, p. 670.

PIPERIDINYL THIACYCLIC DERIVATIVES

This is a division of application Ser. No. 08/281,943, filed Jul. 28, 1994, Pat. No. 5,476,861, which is a division of application Ser. No. 08/201,149, filed Feb. 24, 1994 issued Dec. 6, 1995 U.S. Pat. No. 5,371,093 which is a continuation of application Ser. No 076,268 filed Jun. 11, 1993 now abandoned which is a continuation of application Ser. No. 07/835,658 filed Feb. 13, 1992 now abandoned, which is herein incorporated by reference.

FIELD OF THE INVENTION

The present invention is directed to compounds, pharmaceutical compositions and methods of treatment using same. The compounds of the present invention are piperidinyl thiacyclic derivatives useful in the treatment of allergic diseases and the treatment of diseases responsive to serotonin 5HT2 antagonists.

SUMMARY OF THE INVENTION

The present invention comprises compounds of Formula I:

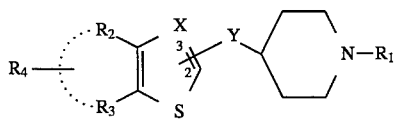

optical isomers or pharmaceutically acceptable salts thereof, wherein

Y is —C(=O)—, —C(=CH$_2$)—, —C(H)(OH)—, —C(OH)(phenyl)— or —C(B)(OH) wherein B is

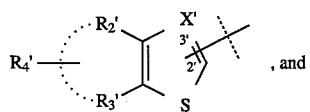, and

Y is attached at the heterocycle positions 2 or 3, or Y is also attached at 2' or 3' when B is present.

X and X' are the same or different and are carbon, CH or nitrogen, provided that when Y is attached at the 3 or 3' position, X and X' are each carbon, and when Y is attached at the 2 or 2' position, X and X' are the same or different and are CH or nitrogen;

$R_1$ is —(CH$_2$)$_n$—Z—(CH$_2$)$_m$COR$_5$, —C(O)R$_8$ or

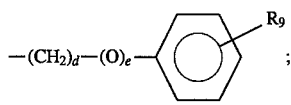;

$R_2$, $R_3$, $R_2'$ and $R_3'$ are the same or different and are hydrogen or C$_{1-4}$ alkyl, or when $R_2$ and $R_3$, and $R_2'$ and $R_3'$ are respectively taken together, with the atoms to which $R_2$ and $R_3$, and $R_2'$ and $R_3'$ are respectively attached, each form a phenyl moiety respectively substituted with $R_4$ or $R_4'$;

Z is a bond, O, or S;

$R_4$ or $R_4'$ are the same or different and are hydrogen, chloro, fluoro, C$_{1-4}$ alkyl, or C$_{1-4}$ alkoxy;

$R_5$ is OH, C$_{1-4}$ alkoxy or —NR$_6$R$_7$;

$R_6$ and $R_7$ are the same or different and are H or C$_{1-4}$ alkyl;

$R_8$ is C$_{1-4}$ alkyl or C$_{1-4}$ alkoxy;

$R_9$ is H, C$_{1-4}$ alkyl, C$_{1-4}$ alkoxy, OH, chloro, bromo, fluoro, —CF$_3$, —NHC(O)R$_{10}$, or CO$_2$R$_{11}$;

$R_{10}$ is C$_{1-4}$ alkyl or C$_{1-4}$ alkoxy;

$R_{11}$ is hydrogen or C$_{1-4}$ alkyl;

n is an integer from 0–3 provided that when Z is not a bond n is an integer from 2–3;

m is an integer from 1 to 3;

d is an integer from 1 to 5; and e is zero or 1 provided that when e is 1:
  d is an integer from 2 to 5; and
  X is N, or $R_2$ and $R_3$, with the atoms to which $R_2$ and $R_3$ are attached, form a phenyl moiety; or X is N, and $R_2$ and $R_3$, with the atoms to which $R_2$ and $R_3$ are attached, form a phenyl moiety.

The present invention further comprises the use of these compounds in a pharmaceutical composition. These compounds are useful in the treatment of subjects having allergic diseases and diseases responsive to 5HT$_2$ antagonism.

DETAILED DESCRIPTION OF THE PRESENT INVENTION

Terms used herein have the following meanings: "C$_{1-4}$ alkyl" is a branched or straight chain alkyl having 1, 2, 3 or 4 carbon atoms such as methyl, ethyl, n-propyl, isopropyl, n-butyl, isobutyl, etc.; "C$_{1-4}$ alkoxy" is a branched or straight chain alkoxy having 1, 2, 3 or 4 carbon atoms such as methoxy, ethoxy, n-propoxy, isopropoxy, n-butoxy, isobutoxy, etc.; and "pharmaceutically acceptable salt" is either an acid addition salt or a basic addition salt.

The compound of Formula I comprises an optionally substituted heterocycle linked to an optionally substituted piperidinyl by a Y group. The Y group represents a carbonyl group (—C(=O)—), an ethenylene group (—C(=CH$_2$)—), a hydroxymethylene group (—C(H)(OH)—), a methine group substituted with hydroxy and phenyl (—C(OH)(phenyl)—) or a methine group substituted with hydroxy and an optionally substituted heterocycle represented by "B" (—C(B)(OH)—). The Y as a carbonyl group is preferred.

As shown in Formula I, Y can be linked to one heterocycle or two of the same or different types of heterocycles (the second heterocycle being B). The heterocycles of the present invention are selected from thienyl (also known as thiophenyl) as in Example 1, thiazolyl as in Example 3, benzothiophenyl as in Example 5 and benzothiazolyl as in Example 8. The heterocycle benzothiazolyl is preferred, and, when two heterocycles are present, they are preferably both not simultaneously thiophenyl.

As shown in formula I, the straight dotted line of B indicates attachment to the remainder of the compound of formula I via the line intersected by the dotted line, the intersected line being between positions 2' and 3' of the heterocycle. The curved dotted line between $R_2$ and $R_3$, and the curved dotted line $R_2$, and $R_3$, each represent a possible ring formation therebetween, as more fully described hereafter.

The heterocycles are attached to Y via the available carbon atom at either the 2 or the 3 position of the heterocycle (see Formula I) or, in the heterocycle designated as "B", the 2' or 3' position, as represented by a line positioned therebetween, provided that when Y is attached at the 3 or 3' position, X and X' are each carbon, and when Y is attached at the 2 or 2' position X and X' are each independently CH or nitrogen. That is, when the heterocycle or heterocycles do not contain a nitrogen in the ring, Y may attach thereto at the 2 or 3 positions (2' or 3' positions in B), but when there is a nitrogen atom at position 3 of the heterocycle, Y will only attach at the 2 position (or the 2' position of B).

The heterocycle or heterocycles attached to Y in Formula I may be optionally substituted. When the heterocycle contains one ring, i.e., a thiophenyl or thiazolyl ring, the substitutions are represented by $R_2$ and $R_3$, or, when the second heterocycle represented by B is present, the substituents are also represented by $R_2'$ and $R_3'$. When the heterocycle(s) contain(s) two rings, i.e., benzothiophenyl or benzothiazolyl, the substitution of the heterocycles is by $R_4$ or $R_4'$, at any position on the phenyl moiety except on the carbon atoms shared with the five membered ring moieties. $R_4$ and $R_4'$ may be the same or different moieties. Each of $R_2$, $R_2'$, $R_3$, or $R_3'$ can be a hydrogen or $C_{1-4}$ alkyl. Preferably, $R_2$, $R_2'$, $R_3$, or $R_3'$ are each hydrogen. Each of $R_4$ or $R_4'$ can be hydrogen, chloro, fluoro, $C_{1-4}$ alkyl or $C_{1-4}$ alkoxy. Preferably, $R_4$ and $R_4'$ are hydrogen.

$R_1$ is attached to the nitrogen in the piperidinyl moiety and may be —$(CH_2)_n$—Z—$(CH_2)_m COR_5$, —$C(O)R_8$ or

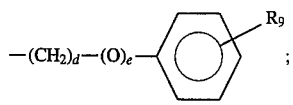

Z is a bond, oxygen atom (O) or sulfur atom (S). When Z is a bond, the subscript n represents the integers 0, 1, 2 or 3. When Z is other than a bond, n represents the integers 2 or 3. The subscript m represents the integer 1, 2 or 3. $R_5$ is —OH, $C_{1-4}$ alkoxy or —$NR_6R_7$. $R_6$ and $R_7$ are each independently hydrogen or $C_{1-4}$ alkyl. The subscript d represents any of the integers 1, 2, 3, 4 or 5, and preferably the integers 1, 2 or 3. The subscript e represents the integers 0 or 1, and preferably 1, with the proviso that both d and e cannot simultaneously be 1. When e is 1, d is greater than 1, i.e., 2, 3, 4 or 5.

Also, when e is 1:
(1) d is an integer from 2 to 5; and
(2)
(a) X is N, or $R_2$ and $R_3$, with the atoms to which $R_2$ and $R_3$ are attached, form a phenyl moiety; or
(b) X is N, and $R_2$ and $R_3$, with the atoms to which $R_2$ and $R_3$ are attached, form a phenyl moiety. In other words, when e is 1, d is always an integer from 2 to 5. Additionally, when e is 1, the heterocycle group shown in Formula I attached Y (not the "B" heterocycle) is not a thiophene radical, i.e., either N is present in the five membered ring and/or a phenyl group is fused to the five membered ring.

$R_8$ means $C_{1-4}$ alkyl or $C_{1-4}$ alkoxy. $R_9$ means H, $C_{1-4}$ alkyl, $C_{1-4}$ alkoxy, OH, chloro, bromo, fluoro, —$CF_3$,—$NHC(O)R_{10}$, or $CO_2R_{11}$. $R_9$ can substitute the phenyl moiety at any ortho, meta or para position, the para position being preferred. $R_{10}$ is $C_{1-4}$ alkyl or $C_{1-4}$ alkoxy, and $R_{11}$ is $C_{1-4}$ alkyl. Preferably $R_9$ is an ester or an acid.

"Pharmaceutically acceptable acid addition salts" applies to any non-toxic organic or inorganic acid addition salt of the base compounds of formula I or any of its intermediates. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono-, di- and tricarboxylic acids.

Illustrative of such acids are, for example, acetic, glycolic, lactic, pyruvic, malonic, succinic, glutaric, fumaric, malic, tartaric, citric, ascorbic maleic, hydroxymaleic, benzoic, hydroxybenzoic, phenylacetic, cinnamic, salicyclic, 2-phenyoxybenzoic, p-toluenesulfonic acid and sulfonic acids such as methanesulfonic acid and 2-hydroxyethane sulfonic acid. Either the mono- or di-acid salts can be formed, and such salts can exist in either a hydrated or substantially anhydrous form. In general, the acid addition salts of these compounds show increased solubility in water and various hydrophilic organic solvents and, in comparison to their free base forms, generally demonstrate higher melting points.

Some of the compounds of Formula I contain asymmetric centers. Any reference in this application, including the claims, to one of the compounds represented by Formula I is meant to encompass either a specific optical isomer or a mixture of enantiomers or diastereomers. The specific optical isomers can be separated and recovered by techniques known in the art such as chromatography on chiral stationary phases or resolution via chiral salt formation and subsequent separation by selective crystallization.

The piperidinyl thiacyclic derivatives of Formula I can be prepared by utilizing conventional procedures and techniques which are well known and appreciated in the art. The schemes show compounds having a connecting line through the heterocycle between positions 2 and 3 of the heterocycle (positions 2 and 3 being designated as in Formula I). This is to indicate attachment at the heterocycle at either position 2 or 3 with the caveat that when X is nitrogen, the heterocycle is always attached at position 2.

One general synthetic procedure for the preparation of the compounds of Formula I wherein Y is —C(=O)— is set forth in Scheme A. In Scheme A, all substituents are as previously defined unless otherwise indicated.

Scheme A

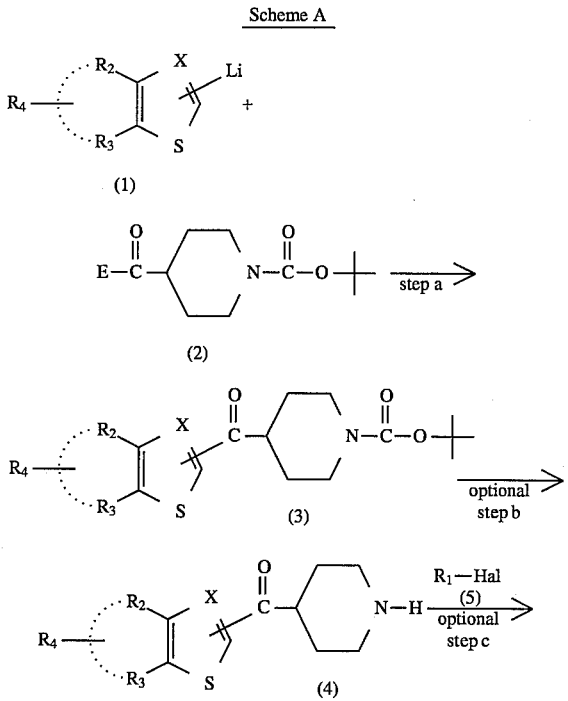

-continued
Scheme A

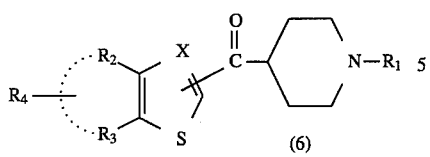

E=$C_1$–$C_4$ alkoxy or $N(OCH_3)CH_3$
Hal=Cl, Br, or I

Scheme A provides one general synthetic procedure for preparing the compounds of Formula I wherein Y is —C(=O)—.

In step a, the appropriate lithio thiacyclic derivative of structure (1) is acylated with the piperidinyl derivative of structure (2) to give the corresponding piperidinyl thiacyclic derivative of structure (3).

For example, a solution of the appropriate lithio thiacyclic derivative of structure (1) is contacted with the piperidinyl derivative of structure (2) at a temperature range of from about −90° C. to about −50° C. and more preferably about −78° C. The reaction is typically conducted under anhydrous conditions in a suitable aprotic organic solvent such as tetrahydrofuran. The piperidinyl derivative and the lithio thiacyclic derivative are preferably present in the reaction zone in an approximately equimolar quantity. A slight excess of either reactant is not deleterious to the reaction. The reaction is allowed to proceed for a period of time ranging from about 20 minutes to about 5 hours, and more preferably about 30 minutes. The reaction is then quenched with a proton source such as, for example, saturated aqueous ammonium chloride or methanol. The resulting reaction mixture is extracted with a suitable solvent, such as ethyl acetate, washed with water, dried over either $Na_2SO_4$ or $MgSO_4$, filtered and the solvent evaporated in vacuo.

Appropriate lithio thiacyclic derivatives of structure (1) are commercially available or prepared by techniques and procedures well known in the art. For example, a solution of the appropriate starting thiacyclic derivative is contacted with an organolithium compound such as n-butyllithium or t-butyllithium, more preferably with t-butyllithium, for a period of time ranging from about 5 minutes to about 30 minutes and more preferably about 15 minutes; at a temperature range of from about −90° C. to about −50° C. and more preferably about −78°C. The organolithium compound will be present in the quantity of from about 1.0 to about 1.1 equivalents for every mole of thiacyclic derivative utilized, and more preferably will be present in an approximately equimolar quantity with the lithio thiacyclic derivative. The reaction is typically conducted under anhydrous conditions in a suitable aprotic organic solvent such as tetrahydrofuran.

Typically, when Y is to be attached at the 3 position of the lithio thiacyclic derivative of structure (1), an appropriate starting thiacyclic derivative is one wherein the 3 position is substituted with bromine or iodine. When Y is to be attached at the 2 position of the lithio thiacyclic derivative of structure (1), an appropriate starting heterocyclic derivative is one wherein the 2 position is substituted with hydrogen, bromine or iodine. Examples of appropriate starting heterocyclic derivatives are 3-bromobenzo[b]thiophene, benzo[b]thiophene, benzothiazole, 2-bromobenzothiazole, thiazole, and 3-bromothiophene.

The piperidinyl heterocyclic derivative of structure (3) can be purified according to techniques known in the art. For example, one suitable technique is to subject the concentrate obtained above to chromatography on silica gel utilizing an appropriate organic solvent such as ethyl acetate as the eluting agent. The eluent can be evaporated and the resulting product can be recrystallized from a suitable solvent such as, for example, cyclohexane. Other suitable solvent systems will be readily apparent to those skilled in the art.

In optional step b, the piperidine functionality of the appropriate piperidinyl thiacyclic derivative of structure (3) is deprotected under acidic conditions to give the piperidinyl thiacyclic derivative of structure (4) using procedures and techniques well known in the art. For example, the t-butyloxycarbonyl group (t-Boc) can be cleaved with trifluoroacetic acid.

In optional step c, the piperidine functionality of the appropriate piperidinyl thiacyclic derivative of structure (4) is N-alkylated under basic conditions with the appropriate alkyl halide of structure (5) to give the piperidinyl thiacyclic derivative of structure (6).

For example, the piperidinyl thiacyclic derivative of structure (4) is reacted with the appropriate alkyl halide of structure (5) in the presence of a base such as $K_2CO_3$, $KHCO_3$, $Na_2CO_3$, $NaHCO_3$, triethylamine, or pyridine in a solvent such as dimethylformamide, dimethylsulfoxide, aqueous tetrahydrofuran or ethanol. Typically the reactants will be stirred together for a period of time ranging from about 30 minutes to about 48 hours, at a temperature range of from about 0° C. to about 100°C. The non-reacting substituents appearing in the alkyl halide ($R_1$) correspond to those appearing in the product. The piperidinyl thiacyclic derivative of structure (6) can be recovered from the reaction zone by treatment with water and extraction with an organic solvent as is known in the art. It can be purified by techniques known in the art such as recrystallization or chromatography as described previously. Typically the piperidinyl thiacyclic derivative of structure (4), as its trifluoroacetic acid salt, is converted in situ to its free base during the alkylation and may be optionally converted to other acid addition salts as is known in the art.

Alternatively, the piperidine functionality of the appropriate piperidinyl thiacyclic derivative of structure (4) can be N-alkylated with the appropriate alkyl halide of structure (5) under phase-transfer catalysis conditions as is known in the art.

Alternatively, those piperidinyl thiacyclic derivatives of structure (6) wherein $R_1$ is —$(CH_2)_n$—Z—$(CH_2)_m COR_5$ wherein $R_5$ is OH or

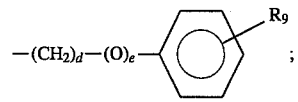

wherein $R_9$ is $CO_2R_{11}$ and $R_{11}$ is H may be prepared from the appropriate piperidinyl thiacyclic derivatives of structure (6) wherein $R_1$ is —$(CH_2)_n$—Z—$(CH_2)_m COR_5$ wherein $R_5$ is $C_{1-4}$ alkoxy or

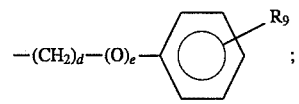

wherein $R_9$ is $CO_2R_{11}$ and $R_{11}$ is $C_{1-4}$ alkyl via an ester hydrolysis reaction as is known in the art.

Starting materials for use in Scheme A are readily available to one of ordinary skill in the art. For example, carbomethoxy methoxyethyl chloride is described in *J. Org. Chem.* 26, 4325–7 1961.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to temperature in degrees Celsius; "mm Hg" refers to pressure in millimeters of mercury; "μL" refers to microliters; "μg" refers to micrograms; and "μM" refers to micromolar.

EXAMPLE 1

4-[(Thiophene-2-yl)carbonyl]-1-piperidinecarboxylic acid, 1,1-dimethylethyl ester

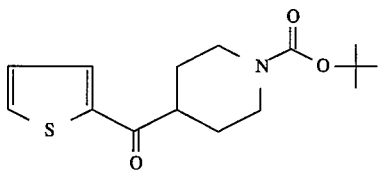

Mix 4-piperidinecarboxylic acid (107.5 g, 832 mmol), 1N sodium hydroxide (40 g in 900 mL water) and tert-butanol (1800 mL). Add, by portionwise addition, di-tert-butyl dicarbonate (200 g, 916 mmol). Stir overnight, evaporate the solvent in vacuo and acidify the aqueous phase with aqueous hydrochloric acid. Extract the acidic aqueous phase with ethyl ether (3×), combine the organic phases and wash with water and brine. Dry (MgSO$_4$), evaporate the solvent in vacuo and recrystallize (ethyl acetate/hexane) to give 1,4-piperidinedicarboxylic acid, 1-(1,1-dimethylethyl) ester as white needles, m.p. 147–149° C.

Dissolve 1,4-piperidinedicarboxylic acid, 1-(1,1-dimethylethyl) ester (50.0 g, 218 mmol) in anhydrous methylene chloride (500 mL) and place under a nitrogen atmosphere. Add, by portionwise addition, 1,1'-carbonyldiimidazole (38.9 g, 240 mmol) and stir for 1 hour.

Add, in one portion, N,O-dimethylhydroxylamine hydrochloride (23.4 g, 240 mmol) and stir overnight. Wash the solution with 1N hydrochloric acid (2X), saturated sodium hydrogen carbonate and brine. Dry (MgSO$_4$), evaporate the solvent in vacuo and purify by distillation to give 4-[[(N-methoxy-N-methyl)amino]carbonyl]-1-piperidinecarboxylic acid, 1,1-dimethylethyl ester as a clear oil, b.p. 120°–140° C. @0.8 mm Hg.

Mix 4-[[(N-methoxy-N-methyl)amino]carbonyl]-1-piperidinecarboxylic acid, 1,1-dimethylethyl ester (3.0 g, 11.02 mmol) and anhydrous tetrahydrofuran (10 mL), cool to −78° C. and place under an argon atmosphere. Add 2-lithiothiophene (12.1 mL of a 1M solution in tetrahydrofuran, 12.1 mmol). Stir the resulting brown solution at −78° C. for 1 hour, remove the ice bath and allow to warm for 15 minutes. Add saturated ammonium chloride (10 mL) and stir for 30 minutes. Partition between ethyl acetate and water, separate the organic phase and wash the aqueous phase with additional ethyl acetate. Wash the combined organic phases with saturated sodium chloride, dry (MgSO$_4$) and evaporate the solvent in vacuo. Purify by silica gel chromatography (20% ethyl acetate/hexane) and recrystallize (ethyl acetate/hexane) to give the title compound as pale yellow crystalline solid; mp 154°–156°C.

Anal. Calcd for C$_{15}$H$_{21}$NO$_3$S: C, 60.99; H, 7.17; N, 4.74. Found: C, 60.89; H, 7.26; N, 4.74.

EXAMPLE 2

(Thiophene-2-yl)(4-piperidinyl)methanone.CF$_3$CO$_2$H

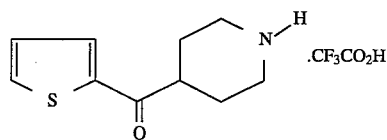

Mix 4-[(thiophene-2-yl)carbonyl]-1-piperidinecarboxylic acid, 1,1-dimethylethyl ester (12.9 g, 43.67 mmol) and trifluoroacetic acid (80 mL) and stir at room temperature for 2 hours. Cool in an ice/water bath and dilute with ethyl ether. Collect the resulting solid by filtration, wash with ethyl acetate and recrystallize (methanol/ethyl ether) to give the title compound as an off-white solid; mp 186°–187°C.

Anal. Calcd for C$_{10}$H$_{13}$NOS.CF$_3$CO$_2$H: C, 46.60; H, 4.56; N, 4.50. Found: C, 46.35; H, 4.56; N, 4.49.

EXAMPLE 3

4-[(2-Thiazolyl)carbonyl]-1-piperidinecarboxylic acid, 1,1-dimethylethyl ester

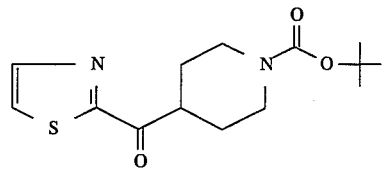

Prepare according the procedure described in Example 1 using 2-lithiothiazole.

EXAMPLE 4

(2-Thiazolyl)(4-piperidinyl)methanone.CF$_3$CO$_2$H

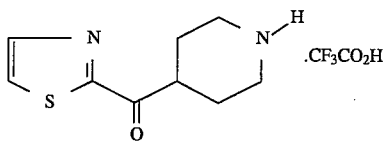

Prepare according to the procedure described in Example 2 using 4-[(2-thiazolyl)carbonyl]-1-piperidinecarboxylic acid, 1,1-dimethylethyl ester.

EXAMPLE 5

4-[(Benzo[b]thiophene-3-yl)carbonyl]-1-piperidinecarboxylic acid, 1,1-dimethylethyl ester

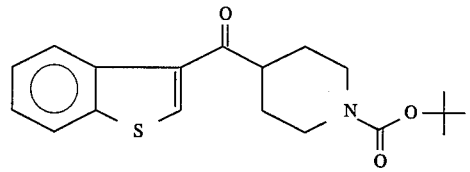

Dissolve benzo[b]thiophene (23 g, 0.170 mmol) in carbon tetrachloride (80 mL). Add, by dropwise addition, a solution of bromine (26.85 g, 0.168 mmol) in carbon tetrachloride (30 mL) and stir at room temperature for 2 days. Quench with a 1M solution of sodium thiosulfate and separate the organic phase. Extract the aqueous phase with carbon tetrachloride, combine the organic phases and dry (MgSO$_4$). Evaporate the solvent in vacuo and purify by distillation to give 3-bromobenzo[b]thiophene as a pale yellow liquid (17.33 g, 48%); bp 64°–72° C. @ 0.02 mm Hg.

Dissolve freshly distilled 3-bromobenzo[b]thiophene (2.47 g, 11.59 mmol) in anhydrous ethyl ether (50 mL), place under an argon atmosphere and cool to −78° C. Add, by dropwise addition, t-butyllithium (13.6 mL of a 1.7M solution in pentane, 23.1 mmol) and stir at −78° C. for 20 minutes. Add, by dropwise addition, a solution of 4-[[(N-methoxy-N-methyl)amino]carbonyl]-1-piperidinecarboxylic acid, 1,1dimethylethyl ester (3.16 g, 11.59 mmol) in anhydrous tetrahydrofuran (15 mL). Stir at −78° C. for 1 hour and quench with saturated ammonium chloride. Partition between water and ethyl acetate, separate the organic phase and extract the aqueous phase with ethyl acetate. Wash the combined organic phases with saturated sodium chloride and dry (Na$_2$SO$_4$). Evaporate the solvent in vacuo and purify by chromatography (20% ethyl acetate/hexane) to give the title compound as a colorless foam.

Mass Spectrum: EI/70EV m/e 345 (M$^{+\cdot}$)

EXAMPLE 6

(Benzo[b]thiophene-3-yl)(4-piperidinyl)methanone. CF$_3$CO$_2$H

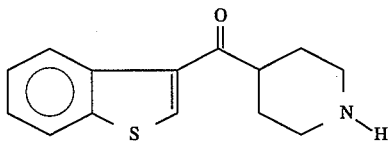

Dissolve 4-[(benzo[b]thiophene-3-yl)carbonyl]-1-piperidinecarboxylic acid, 1,1-dimethylethyl ester (3.75 g, 10.8 mmol) in trifluoroacetic acid (30 mL). Stir at room temperature for 30–40 minutes. Cool in an ice bath and dilute with ethyl ether (200 mL). Keep at 0° C. for 1–2 hours, collect the solid by filtration and recrystallize (methanol/ethyl ether) to give the title compound as small colorless plates; mp 195°–197° C.

Anal. Calcd for C$_{14}$H$_{15}$NOS. CF$_3$CO$_2$H: C, 53.48; H, 4.49; N, 3.90. Found: C, 53.14; H, 4.50; N, 3.90.

EXAMPLE 7

[Benzo[b]thiophene-3-yl][1-[2-(4-methoxyphenyl)-ethyl]-4-piperidinyl]methanone

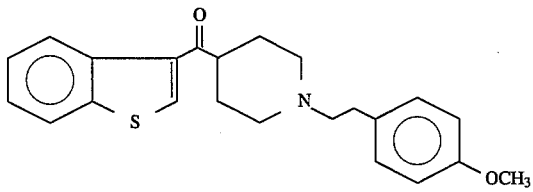

Mix (benzo[b]thiophene-3-yl)(4-piperidinyl)methanone. CF$_3$CO$_2$H (2.0 g, 5.56 mmol), 2-(4-methoxyphenyl)ethyl bromide (1.27 g, 5.93 mmol), potassium carbonate (1.95 g, 1.41 mmol) and anhydrous dimethylformamide (20 mL). Warm to approximately 90° C. and stir overnight. Allow to cool to room temperature and partition between a 2:1 mixture of ethyl acetate:toluene and water. Separate the aqueous phase and wash the organic phase with water and saturated sodium chloride. Dry (Na$_2$SO$_4$) and evaporate the solvent in vacuo. Purify by chromatography (40% ethyl acetate/hexane) and recrystallize (cyclohexane) to give the title compound as pale yellow plates; mp 114°–116° C.

Anal. Calcd for C$_{23}$H$_{25}$NO$_2$S: C, 72.79;H, 6.64; N, 3.69. Found: C, 72.58; H, 6.63; N, 3.66.

EXAMPLE 8

4-[(2-Benzothiazolyl)carbonyl]-1-piperidinecarboxylic acid, 1,1-dimethylethyl ester

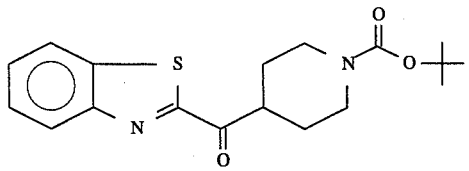

Dissolve benzothiazole (2.0 g, 14.79 mmol) in anhydrous tetrahydrofuran (50 mL), place under an argon atmosphere and cool to −78° C. Add, by dropwise addition, n-butyllithium (6.5 mL of a 2.5M solution in hexane, 16.27 mmol) and stir at −78° C. for 30 minutes. Add, by dropwise addition, a solution of 4-[[(N-methoxy-N-methyl)amino]carbonyl]-1-piperidinecarboxylic acid, 1,1-dimethylethyl ester (4.03 g, 14.79 mmol) in anhydrous tetrahydrofuran (50 mL). Stir at −78° C. for 1.5 hours, remove the ice bath and allow to warm for 10 minutes, quench with saturated ammonium chloride (100 mL) and stir for an additional hour. Separate the organic phase and extract the aqueous phase with ethyl acetate. Combine the organic phases, dry (MgSO$_4$) and evaporate the solvent in in vacuo. Purify by chromatography (10% ethyl acetate/hexane) to give the title compound as pale yellow crystals; mp 94°–95° C.

Anal. Calcd for C$_{18}$H$_{22}$N$_2$O$_3$S: C, 62.40; H, 6.40; N, 8.09. Found: C, 62.20; H, 6.46; N, 7.94.

EXAMPLE 9

(2-Benzothiazolyl)(4-piperidinyl)methanone. CF$_3$CO$_2$H

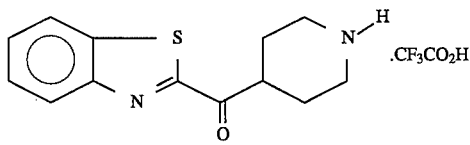

Mix 4-[(2-benzothiazolyl)carbonyl]-1-piperidinecarboxylic acid, 1,1-dimethylethyl ester (10.5 g, 30.31 mmol) and trifluoroacetic acid (75 mL) and stir at room temperature for 2 hours. Cool in an ice/water bath and add ethyl ether until a solid begins to precipitate. Stir at 0° C. for 30 minutes, collect the solid by filtration and wash with ethyl ether and recrystallize (methanol/ethyl ether) to give the title compound as a white powder; mp 195°–197° C.

Anal. Calcd for C$_{13}$H$_{14}$N$_2$OS. CF$_3$CO$_2$H: C, 50.00; H, 4.20; N, 7.77. Found: C, 50.12; H, 4.17; N, 7.79.

EXAMPLE 10

[2-Benzothiazolyl][1-[2-(4-methoxyphenyl)ethyl]-4piperidinyl]methanone

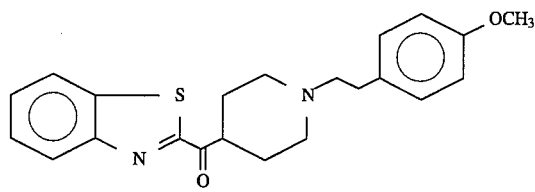

Mix (2-benzothiazolyl)(4-piperidinyl)methanone CF$_3$CO$_2$H (331 g, 9.19 mmol), 2-(4-methoxyphenyl)ethyl bromide (2.07 g, 9.64 mmol), potassium carbonate (3.33 g, 24.1 mmol) and dimethylformamide (35 mL) and heat at 90° C. overnight. Cool to room temperature and partition between a 2:1 mixture of ethyl acetate/toluene and water. Separate the aqueous phase and wash the organic phase with water and brine. Dry (MgSO$_4$) and evaporate the solvent in vacuo. Purify by chromatography (30% ethyl acetate/hexane) and recrystallize (cyclohexane) to give the title compound as a tan powder; mp 119°–120° C.

Anal. Calcd for C$_{22}$H$_{24}$N$_2$O$_2$S: C, 69.44; H, 6.36; N, 7.36. Found: C, 69.48; H, 6.52; N, 7.06. Example 44 gives an alternative method of making this compound.

EXAMPLE 11

[2-Benzothiazolyl][1-[2-(4-fluorophenyl)ethyl]-4-piperidinyl]methanone

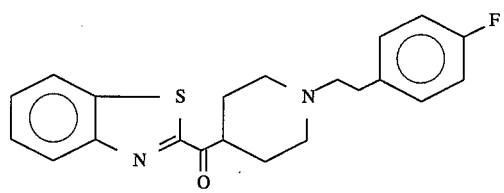

Mix (2-benzothiazolyl)(4-piperidinyl)methanone. CF$_3$CO$_2$H (1.95 g, 5.43 mmol), 2-(4-fluorophenyl)ethyl bromide (1.70 g, 8.35 mmol), benzyltriethylammonium bromide (149 mg, 0.54 mmol), sodium hydroxide (5 g), water (25 mL) and methylene chloride (25 mL). Stir at room temperature under an argon atmosphere overnight, then heat at reflux overnight. Cool the reaction to room temperature, separate the organic phase and extract the aqueous phase with methylene chloride (50 mL). Combine the organic phases, dry (Na$_2$SO$_4$) and evaporate the solvent in vacuo. Purify by chromatography (20% ethyl acetate/hexane with 2% triethylamine) and recrystallize (hexane) to give the title compound as pale yellow needles; mp 97°–98° C.

Anal. Calcd for C$_{21}$H$_{21}$FN$_2$OS: C, 68.45; H, 5.74; N, 7.60. Found: 68.26; H, 5.58; N, 7.29.

EXAMPLE 12

[2-Benzothiazolyl][1-(2-phenylethyl)-4-piperidinyl]methanone

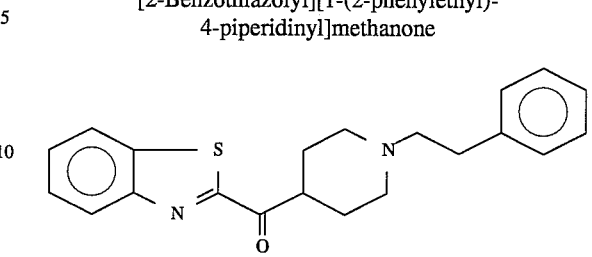

Mix (2-benzothiazolyl)(4-piperidinyl)methanone.CF$_3$CO$_2$H (2.56 g, 7.13 mmol), 2-phenylethyl bromide (1.45 g, 7.84 mmol), 18-Crown-6 (188 mg, 0.71 mmol), potassium carbonate (9.85 g, 71.3 mmol) and methylene chloride (100 mL). Stir at room temperature under an argon atmosphere for 2 hours, then add potassium iodide (200 mg). Stir at room temperature for an additional 2 hours then heat at reflux overnight. Add additional 2-phenylethyl bromide (1.45 g, 7.84 mmol) and heat at reflux overnight. Add additional 2-phenylethyl bromide (1.45 g, 7.84 mmol) and heat at reflux overnight. Cool the reaction to room temperature and pour into water (150 mL). Separate the organic phase, wash with water (100 mL) and dry (Na$_2$SO$_4$). Evaporate the solvent in vacuo and purify by chromatography (20% ethyl acetate/hexane with 2% triethylamine) to give the title compound as a yellow solid; mp 108.5°–109.5° C.

Anal. Calcd for C$_{21}$H$_{22}$N$_2$OS: C, 71.97; H, 6.33; N, 8.00. Found: C, 71.94; H, 6.22; N, 7.74.

EXAMPLE 13

4-[(2-Benzothiazolyl)carbonyl]-1-piperidineacetic acid, methyl ester.HCl

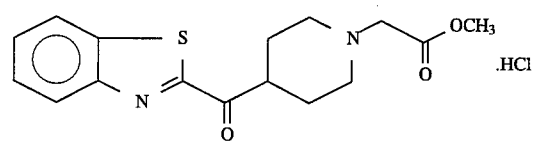

Mix (2-benzothiazolyl)(4-piperidinyl)methanone.CF$_3$CO$_2$H (3.0 g, 8.33 mmol), methyl bromoacetate (1.34 g, 8.74 mmol), sodium bicarbonate (1.75 g, 20.83 mmol), tetrahydrofuran (120 mL) and water (30 mL). Heat at reflux for 4 hours, cool to room temperature and partition between ethyl acetate and water. Separate the organic phase and extract the aqueous phase with ethyl acetate. Combine the organic phases, wash with water and dry (MgSO$_4$). Evaporate the solvent in vacuo to give a yellow oil. Dissolve the oil in ethanol/ethyl ether and treat with ethereal hydrogen chloride gas. Cool overnight, collect the resulting solid by filtration, wash with ethyl ether and dry to give the title compound as a white crystalline solid; mp 177°–178° C.

Anal. Calcd for C$_{16}$H$_{18}$N$_2$ O$_3$ S.HCl: C, 54.16; H, 5.40; N, 7.89. Found: C, 53.87; H, 5.41; N, 8.06.

EXAMPLE 14

4-[3-[4-[(2-Benzothiazolyl)carbonyl]-1piperidinyl]-propoxy]benzoic acid, methyl ester

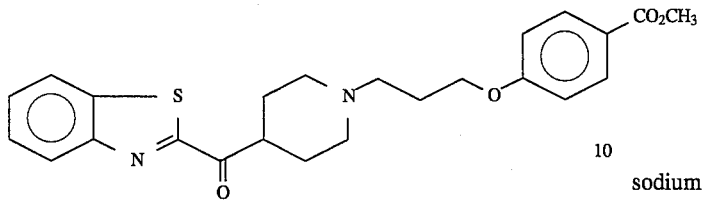

Dissolve 4-(3-chloropropoxy)benzoic acid, methyl ester (6.97 g, 30.5 mmol) in anhydrous acetone (100 mL) and add powdered sodium iodide (16.0 g, 107 mmol). Heat at reflux under an argon atmosphere for 38 hours. Dilute with ethyl ether (100 mL) and filter through Celite® filter aid. Wash the filtrate with water and brine, then dry ($MgSO_4$). Evaporate the solvent in vacuo to give 4-(3iodopropoxy)benzoic acid, methyl ester as a yellow oil.

Mix (2-benzothiazolyl)(4-piperidinyl)methanone.$CF_3CO_2H$ (7.08 g, 19.7 mmol), 4-(3-iodopropoxy)benzoic acid, methyl ester (6.50 g, 20.3 mmol), sodium hydrogen carbonate (3.41 g, 40.6 mmol), tetrahydrofuran (100 mL) and water (20 mL). Heat at reflux under an argon atmosphere overnight. Cool to room temperature, dilute with ethyl acetate (150 mL), wash with 10% sodium hydrogen carbonate (50 mL), water (2×50 mL) and saturated sodium chloride (50 mL). Dry ($MgSO_4$), evaporate the solvent in vacuo and triturate with hexane. Collect the solid by filtration and recrystallize (methanol) to give the title compound as a pale yellow solid; mp 108°–109.5° C.

Anal. Calcd for $C_{24}H_{26}N_2O_4S$: C, 65.73; H, 5.98; N, 6.39. Found: C, 65.44; H, 6.06; N, 6.34.

EXAMPLE 15

[2-Benzothiazolyl][1-[3-(4-methoxyphenyl)propoxy]-4-piperidinyl]methanone

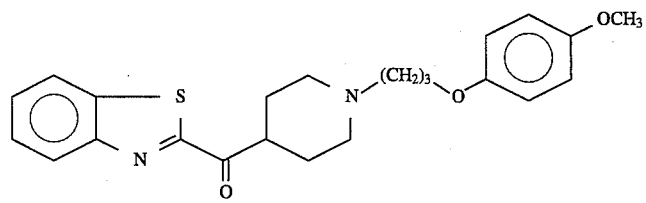

Mix (2-benzothiazolyl)(4-piperidinyl)methanone.$CF_3CO_2H$ (7.0 g, 19.5 mmol), 1-(3-chloropropoxy)-4-methoxybenzene (4.01 g, 20.0 mmol), sodium bicarbonate (3.36 g, 40.0 mmol), sodium iodide (3.04 g, 20.3 mmol), tetrahydrofuran (100 mL) and water (20 mL). Place under an argon atmosphere and heat at reflux for 24 hours. Dilute with ethyl acetate (100 mL) and wash with water (50 mL) and brine (50 mL). Dry ($MgSO_4$), evaporate the solvent in vacuo to give an yellow solid Purify by chromatography (ethyl acetate) and recrystallize (ethanol) to give the title compound as a pale yellow solid; mp 114°–115° C.

Anal. Calcd for $C_{23}H_{26}N_2O_3S$: C, 67.29; H, 6.38; N, 6.82. Found: C, 67.12; H, 6.44; N, 6.67.

EXAMPLE 16

4-[5-[4-[(2-Benzothiazolyl)carbonyl]-1-piperidinyl]-pentoxy]benzoic acid, methyl ester

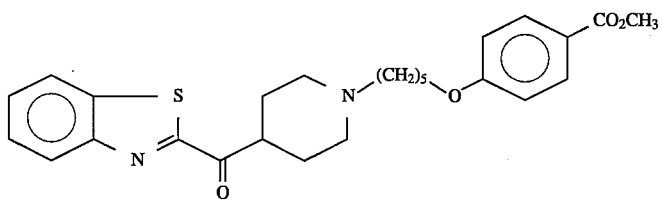

Prepare according to the procedure described in Example 15 using 4-(5-chloropentoxy)benzoic acid, methyl ester. 4-(5Chloropentoxy)benzoic acid, methyl ester can be prepared from methyl 4-hydoxybenzoate and 1,3-dibromopropane according the procedure described in *J. Am. Chem. Soc.* 44, 2645 1922.

EXAMPLE 17

[2-Benzothiazolyl][1-[3-(4-hydroxyphenyl)propoxy]-4-piperidinyl]methanone

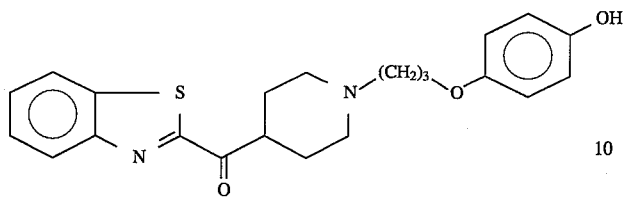

Prepare according to the procedure described in Example 15 using 1-(3-chloropropoxy)-4-hydroxybenzene. 1-(3-Chloropropoxy)-4-hydroxybenzene can be prepared by treating 1-(3-chloropropoxy)-4-methoxybenzene with trimethylsilyl iodide according the procedure described in *J. Org. Chem.* 42, 3761 1977.

EXAMPLE 18

[2-Benzothiazolyl][1-[3-(3-methylphenyl)propoxy]-4-piperidinyl]methanone

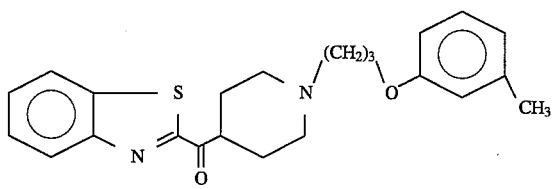

Prepare according to the procedure described in Example 15 using 1-(3-chloropropoxy)-3-methylbenzene. 1-(3-Chloropropoxy)-3-methylbenzene can be prepared from m-cresol and 1,3-dibromopropane according the procedure described in *J. Am. Chem. Soc.* 44, 2645 1922.

EXAMPLE 19

[2-Benzothiazolyl][1-[3-(4-fluorophenyl)propoxy]-4-piperidinyl]methanone

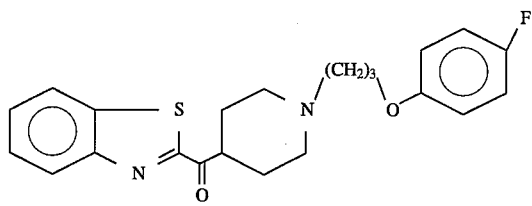

Prepare according to the procedure described in Example 15 using 1-(3-chloropropoxy)-4-fluorobenzene.

EXAMPLE 20

[2-Benzothiazolyl][1-[3-(4-acetamidophenyl)propoxy]-4-piperidinyl]methanone

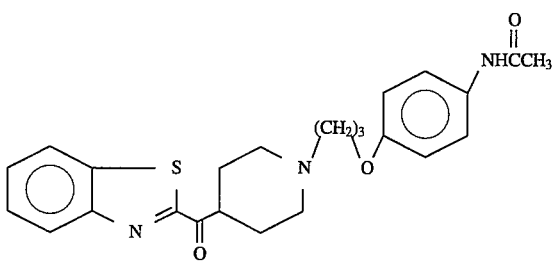

Mix (2-benzothiazolyl)(4-piperidinyl)methanone.$CF_3CO_2H$ (3.45 g, 9.6 mmol), 1-(3-chloropropoxy)-4-acetamidobenzene (2.20 g, 9.66 mmol), sodium bicarbonate (1.68 g, 20.0 mmol), sodium iodide (1.50 g, 10.0 mmol ), tetrahydrofuran (100 mL) and water (20 mL). Place under an argon atmosphere and heat at reflux for 24 hours. Dilute with ethyl acetate (100 mL) and wash with water (50 mL) and brine (50 mL). Dry ($MgSO_4$), evaporate the solvent in vacuo to give a pale yellow solid. Purify by recrystallization (ethanol) to give the title compound as a pale yellow solid; mp 171°–172° C.

Anal. Calcd for $C_{24}H_{27}N_3O_3S$: C, 65.88; H, 6.22; N, 9.60. Found: C, 65.62; H, 6.22; N, 9.60.

EXAMPLE 21

[(2-(4-Chlorobenzothiazolyl))carbonyl]-1-piperidinecarboxylic acid, 1,1-dimethylthyl ester

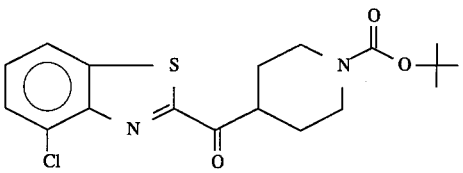

Slurry 2-amino-4-chlorobenzothiazole (0.255 mol) in water (325 mL), heat to reflux and add 48% hydrobromic acid (130 mL). Maintain at reflux for 20 minutes, cool to 0° C. and add a solution of sodium nitrite (17.56 g, 0.255 mol) in water (90 mL), maintaining a temperature of 0° C. Stir at 0° C. for 15 minutes and add by dropwise addition (while keeping cold) to a rapidly stirring mixture of copper (I) bromide (42.03 g, 0.293 mol) in 48% hydrobromic acid (86 mL) and water (225 mL). Stir at room temperature for 20 minutes and then heat on a steam bath for an additional 20 minutes. Allow to stand overnight, extract into methylene chloride and dry ($MgSO_4$). Evaporate the solvent in vacuo and purify by chromatography to give 2-bromo-4-chlorobenzothiazole.

Dissolve 2-bromo-4-chlorobenzothiazole (14.79 mmol) in anhydrous tetrahydrofuran (50 mL), place under an argon atmosphere and cool to −78° C. Add, by dropwise addition, n-butyllithium (6.5 mL of a 2.5M solution in hexane, 16.27 mmol) and stir at −78° C. for 30 minutes. Add, by dropwise addition, a solution of 4-[[(N-methoxy-N-methyl)amino]carbonyl]-1-piperidinecarboxylic acid, 1,1dimethylethyl ester (4.03 g, 14.79 mmol) in anhydrous tetrahydrofuran (50 mL). Stir at −78° C. for 1.5 hours, remove the ice bath and allow to warm for 10 minutes, quench with saturated ammonium chloride (100 mL) and stir for an additional hour. Separate the organic phase and extract the aqueous phase with ethyl acetate. Combine the organic phases, dry (MgSO$_4$) and evaporate the solvent in vacuo. Purify by chromatography to give the title compound.

EXAMPLE 22

[2-(4-Chlorobenzothiazolyl)](4-piperidinyl)-methanone.CF$_3$CO$_2$H

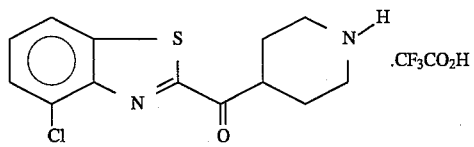

Mix 4-[(2-(4-chlorobenzothiazolyl))carbonyl]-1-piperidinecarboxylic acid, 1,1-dimethylethyl ester (30.31 mmol) and trifluoroacetic acid (75 mL) and stir at room temperature for 2 hours. Cool in an ice/water bath and add ethyl ether until a solid begins to precipitate. Stir at 0° C. for 30 minutes, collect the solid by filtration and wash with ethyl ether to give the title compound.

EXAMPLE 23

[2-(4-Chlorobenzothiazolyl)][1-[2-(4-methoxyphenyl)-ethyl]-4-piperidinyl]methanone

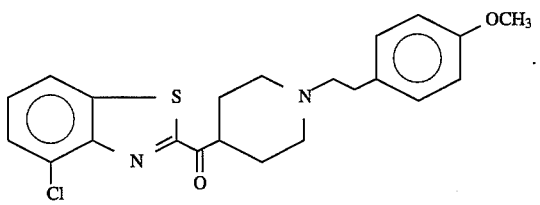

Mix [2-(4-chlorobenzothiazolyl)](4-piperidinyl)methanone.CF$_3$CO$_2$H (9.19 mmol), 2-(4methoxyphenyl)ethyl bromide (2.07 g, 9.64 mmol), potassium carbonate (3.33 g, 24.1 mmol) and dimethylformamide (35 mL) and heat at 90° C. overnight. Cool to room temperature and partition between a 2:1 mixture of ethyl acetate/toluene and water. Separate the aqueous phase and wash the organic phase with water and brine. Dry (MgSO$_4$) and evaporate the solvent in vacuo. Purify by chromatography to give the title compound.

EXAMPLE 24

[(2-(6-Methoxybenzothiazolyl))carbonyl]-1-piperidinecarboxylic acid, 1,1-dimethylethyl ester

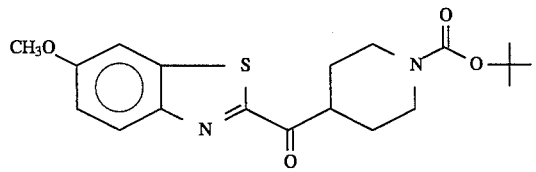

Slurry 2-amino-6-methoxybenzothiazole (0.255 mol) in water (325 mL), heat to reflux and add 48% hydrobromic acid (130 mL). Maintain at reflux for 20 minutes, cool to 0° C. and add a solution of sodium nitrite (17.56 g, 0.255 mol) in water (90 mL), maintaining a temperature of 0° C. Stir at 0° C. for 15 minutes and add by dropwise addition (while keeping cold) to a rapidly stirring mixture of copper (I) bromide (42.03 g,0.293 mol) in 48% hydrobromic acid (86 mL) and water (225 mL). Stir at room temperature for 20 minutes. Allow to stand overnight, extract into methylene chloride and dry (MgSO$_4$). Evaporate the solvent in vacuo and purify by chromatography to give 2-bromo-6-methoxy-benzothiazole.

Dissolve 2-bromo-6-methoxybenzothiazole (14.79 mmol) in anhydrous tetrahydrofuran (50 mL), place under an argon atmosphere and cool to −78° C. Add, by dropwise addition, n-butyllithium (6.5 mL of a 2.5M solution in hexane, 16.27 mmol) and stir at −78° C. for 30 minutes. Add, by dropwise addition, a solution of 4-[[(N-methoxy-N-methyl)amino]carbonyl]-1-carbonyl]-1-piperidinecarboxylic acid, 1-dimethylethyl ester (4.03 g, 14.79 mmol) in anhydrous tetrahydrofuran (50 mL). Stir at −78° C. for 1.5 hours, remove the ice bath and allow to warm for 10 minutes, quench with saturated ammonium chloride (100 mL) and stir for an additional hour. Separate the organic phase and extract the aqueous phase with ethyl acetate. Combine the organic phases, dry (MgSO$_4$) and evaporate the solvent in vacuo. Purify by chromatography to give the title compound.

EXAMPLE 25

[2-(6-Methoxybenzothiazolyl)](4-piperidinyl)-methanone.CF$_3$CO$_2$H

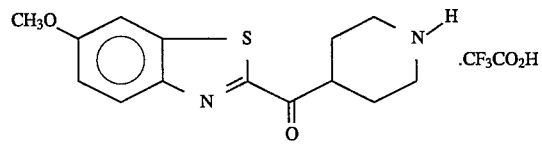

Mix 4-[(2-(6-methoxybenzothiazolyl))carbonyl]-1-piperidinecarboxylic acid, 1,1-dimethylethyl ester (30.31 mmol) and trifluoroacetic acid (75 mL) and stir at room temperature for 2 hours. Cool in an ice/water bath and add ethyl ether until a solid begins to precipitate. Stir at 0° C. for 30 minutes, collect the solid by filtration and wash with ethyl ether to give the title compound.

EXAMPLE 26

4-[3-[4[[2-(6-Methoxybenzothiazolyl)]carbonyl]-1-piperidinyl]propoxy]benzoic acid, methyl ester

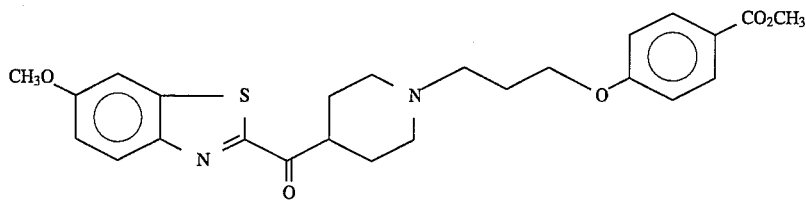

Mix [2-(6-methoxybenzothiazolyl)](4-piperidinyl)methanone.CF$_3$CO$_2$H(9.19 mmol), 3-(4-methoxyphenyl)propyl bromide (9.64 mmol), potassium carbonate (3.33 g, 24.1 mmol) and dimethylformamide (35 mL) and heat at 90° C. overnight. Cool to room temperature and partition between a 2:1 mixture of ethyl acetate/toluene and water. Separate the aqueous phase and wash the organic phase with water and brine. Dry (MgSO$_4$) and evaporate the solvent in vacuo. Purify by chromatography to give the title compound.

EXAMPLE 27

4-[3-[4-[[2-(6-Methoxybenzothiazolyl)]carbonyl]-1-piperidinyl]propoxy]benzoic acid

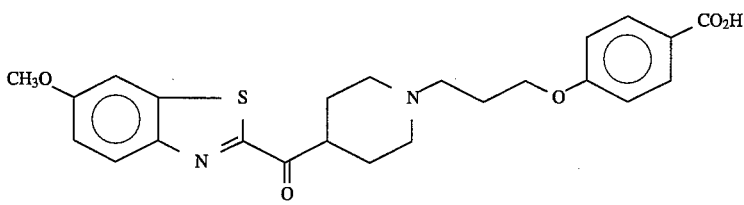

Dissolve 4-[3-[4-[[2-(6-methoxybenzothiazolyl)]carbonyl]-1-piperidinyl]propoxy]benzoic acid, methyl ester (0.233 mmol) in ethanol (4 mL) and treat with lithium hydroxide (42 mg, 10 mmol) and water (1 mL). Stir under nitrogen atmosphere until hydrolysis is complete, evaporate the solvent, acidify with dilute hydrochloric acid and extract the aqueous phases with ethyl acetate (2×). Wash the combined organic phases with water, then with saturated sodium chloride. Dry (MgSO$_4$), evaporate the solvent in vacuo and purify by silica gel chromatography to give the title compound.

EXAMPLE 28

[(2-(6-Fluorobenzothiazolyl))carbonyl]-1-piperidinecarboxylic acid, 1,1-dimethylethyl ester

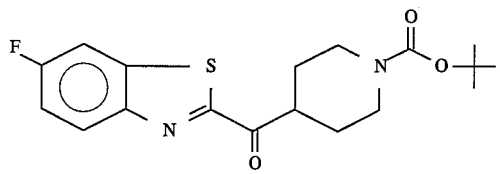

Slurry 2-amino-6-fluorobenzothiazole (0.255 mol) in water (325 mL), heat to reflux and add 48% hydrobromic acid (130 mL). Maintain at reflux for 20 minutes, cool to 0° C. and add a solution of sodium nitrite (17.56 g, 0.255 mol) in water (90 mL), maintaining a temperature of 0° C. Stir at 0° C. for 15 minutes and add by dropwise addition (while keeping cold) to a rapidly stirring mixture of copper (I) bromide (42.03 g,0.293 mol) in 48% hydrobromic acid (86 mL) and water (225 mL). Stir at room temperature for 20 minutes. Allow to stand overnight, extract into methylene chloride and dry (MgSO$_4$). Evaporate the solvent in vacuo and purify by chromatography to give 2-bromo-6fluorobenzothiazole.

Dissolve 2-bromo-6-fluorobenzothiazole (14.79 mmol) in anhydrous tetrahydrofuran (50 mL), place under an argon atmosphere and cool to −78° C. Add, by dropwise addition, n-butyllithium (6.5 mL of a 2.5M solution in hexane, 16.27 mmol) and stir at −78°°C. for 30 minutes. Add, by dropwise addition, a solution of 4-[[(N-methoxy-N-methyl)amino]carbonyl]-1-piperidinecarboxylic acid, 1,1dimethylethyl ester (4.03 g, 14.79 mmol) in anhydrous tetrahydrofuran (50 mL). Stir at −78° C. for 1.5 hours, remove the ice bath and allow to warm for 10 minutes, quench with saturated ammonium chloride (100 mL) and stir for an additional hour. Separate the organic phase and extract the aqueous phase with ethyl acetate. Combine the organic phases, dry (MgSO$_4$) and evaporate the solvent in vacuo. Purify by chromatography to give the title compound.

EXAMPLE 29

[2-(6-Fluorobenzothiazolyl)](4-piperidinyl)-methanone.CF$_3$CO$_2$H

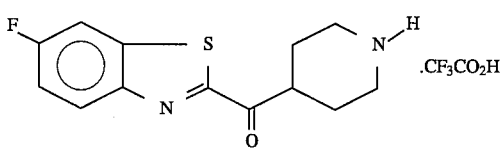

Mix 4-[(2-(6-fluorobenzothiazolyl))carbonyl]-1-piperidinecarboxylic acid, 1,1-dimethylethyl ester (30.31 mmol) and trifluoroacetic acid (75 mL) and stir at room temperature for 2 hours. Cool in an ice/water bath and add ethyl ether until a solid begins to precipitate. Stir at 0° C. for 30 minutes, collect the solid by filtration and wash with ethyl ether to give the title compound.

EXAMPLE 30

2-[4-[[2-(6-Fluorobenzothiazolyl)]carbonyl]-1-piperidinyl]ethoxy]acetic acid, methyl ester Mix [2-(6-fluorobenzothiazolyl)](4-piperidinyl)methanonee.CF$_3$CO$_2$H(9.19 mmol), carbomethoxy methoxyethyl chloride (9.64 mmol), potassium carbonate (3.33 g, 24.1 mmol) and dimethylformamide (35 mL) and heat at 90° C. overnight. Cool to room temperature and partition between a 2:1 mixture of ethyl acetate/toluene and water. Separate the aqueous phase and wash the organic phase with

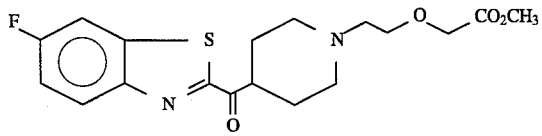

water and brine. Dry (MgSO$_4$) and evaporate the solvent in vacuo. Purify by chromatography to give the title compound.

EXAMPLE 31

2-[4-[[2-(6-Fluorobenzothiazolyl)]carbonyl]-1-piperidinyl]ethoxy]acetic acid

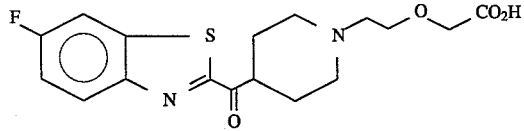

Dissolve 2-[4-[[2-(6-fluorobenzothiazolyl)]carbonyl]-1-piperidinyl]ethoxy]acetic acid, methyl ester (0.233 mmol) in ethanol (4 mL) and treat with lithium hydroxide (42 mg, 10 mmol) and water (1 mL). Stir under nitrogen atmosphere until hydrolysis is complete, evaporate the solvent, acidify with dilute hydrochloric acid and extract the aqueous phases with ethyl acetate (2×). Wash the combined organic phases with water, then with saturated sodium chloride. Dry (MgSO$_4$), evaporate the solvent in vacuo and purify by silica gel chromatography to give the title compound.

The following compounds can be prepared according to the procedures described above in Examples 1–31:
2-[4-[[2-(4-Chlorobenzothiazolyl)]carbonyl]-1-piperidinylethoxy]acetic acid, methyl ester;
2-[4-[[2-(4-Chlorobenzothiazolyl)]carbonyl]-1-piperidinyl] ethoxyacetic acid;
[2-(4-Chlorobenzothiazolyl)][1-[2-(4-methoxyphenyl)ethyl] -4-piperidinyl]methanone;
4-3-4-[[2-(4-Chlorobenzothiazolyl)]carbonyl]-1-piperidinyl]propoxy]benzoic acid, methyl ester;
4-3-[4-[[2-(4-Chlorobenzothiazolyl)]carbonyl]-1-piperidinyl]propoxy]benzoic acid;
2-[4-[[2-(4-Methoxybenzothiazolyl)]carbonyl]-1-piperidinyl]ethoxyacetic acid, methyl ester;
2-[4-[[2-(4-Methoxybenzothiazolyl)]carbonyl]-1-piperidinyl]ethoxyacetic acid;
[2-(4-Methoxybenzothiazolyl)][1-[2-(4-methoxyphenyl)ethyl]-4-piperidinyl]methanone;
4-3-[4-[[2-(4-Methoxybenzothiazolyl)]carbonyl]-1-piperidinyl]propoxy]benzoic acid, methyl ester;
4-[3-[4-[[2-(4-Methoxybenzothiazolyl)]carbonyl]-1-piperidinyl]propoxy]benzoic acid;
2-[4-[[2-(6-Methoxybenzothiazolyl)]carbonyl]-1-piperidinyl]ethoxyacetic acid, methyl ester;
2-[4-[[2-(6-Methoxybenzothiazolyl)]carbonyl]-1-piperidinyl]ethoxyacetic acid;
[2-(6-Methoxybenzothiazolyl)][1-[2-(4-methoxyphenyl)ethyl]-4-piperidinyl]methanone;
4-[3-[4-[[2-(6-Methoxybenzothiazolyl)]carbonyl]-1-piperidinyl]propoxy]benzoic acid, methyl ester;
4-[3-[4-[[2-(6-Methoxybenzothiazolyl)]carbonyl]-1-piperidinyl]propoxy]benzoic acid;
2-[4-[[2-(4-Methylbenzothiazolyl)]carbonyl]-1-piperidinyl] ethoxyacetic acid, methyl ester;
2-[4-[[2-(4-Methylbenzothiazolyl)]carbonyl]-1-piperidinyl] ethoxyacetic acid;
[2-(4-Methylbenzothiazolyl)][1-[2-(4-methoxyphenyl)ethyl] -4-piperidinyl]methanone;
4-[3-[4-[[2-(4-Methylbenzothiazolyl)]carbonyl]-1-piperidinyl]propoxy]benzoic acid, methyl ester;
4-[3-[4-[[2-(4-Methylbenzothiazolyl)]carbonyl]-1-piperidinyl]propoxy]benzoic acid;
2-[4-[[2-(6-Methylbenzothiazolyl)]carbonyl]-1-piperidinyl] ethoxyacetic acid, methyl ester;
2-[4-[[2-(6-Methylbenzothiazolyl)]carbonyl]-1-piperidinyl] ethoxyacetic acid;
[2-(6-Methylbenzothiazolyl)][1-[2-(4-methoxyphenyl)ethyl] -4-piperidinyl]methanone;
4-[3-[4-[[2-(6-Methylbenzothiazolyl)]carbonyl]-1-piperidinyl]propoxy]benzoic acid, methyl ester;
4-[3-[4-[[2-(6-Methylbenzothiazolyl)]carbonyl]-1-piperidinyl]propoxy]benzoic acid;
2-[4-[[2-(6-Fluorobenzothiazolyl)]carbonyl]-1-piperidinyl] ethoxyacetic acid, methyl ester;
2-[4-[[2-(6-Fluorobenzothiazolyl)]carbonyl]-1-piperidinyl] ethoxyacetic acid;
[2-(6-Fluorobenzothiazolyl)][1-[2-(4-methoxyphenyl)ethyl]-4-piperidinyl]methanone;
4-[3-[4-[[2-(6-Fluorobenzothiazolyl)]carbonyl]-1-piperidinyl]propoxy]benzoic acid, methyl ester;
4-[3-[4-[[2-(6-Fluorobenzothiazolyl)]carbonyl]-1-piperidinyl]propoxy]benzoic acid;
2-[4-[[2-(6-Chlorobenzothiazolyl)]carbonyl]-1-piperidinyl] ethoxyacetic acid, methyl ester;
2-[4-[[2-(6-Chlorobenzothiazolyl)]carbonyl]-1-piperidinyl] ethoxyacetic acid;
[2-(6-Chlorobenzothiazolyl)][1-[2-(4-methoxyphenyl)ethyl] -4-piperidinyl]methanone;
4-[3-[4-[[2-(6-Chlorobenzothiazolyl)]carbonyl]-1-piperidinyl]propoxy]benzoic acid, methyl
4-[3-[4-[[2-(6-Chlorobenzothiazolyl)]carbonyl]-1-piperidinyl]propoxy]benzoic acid.

A general synthetic procedure for the preparation of the compounds of Formula I wherein Y is —C(=CH$_2$)=, —C(H)(OH)—, —C(OH)(phenyl)— or —C(B)(OH)— is set forth in Scheme B. In Scheme B, all substituents are as previously defined unless otherwise indicated.

Scheme B

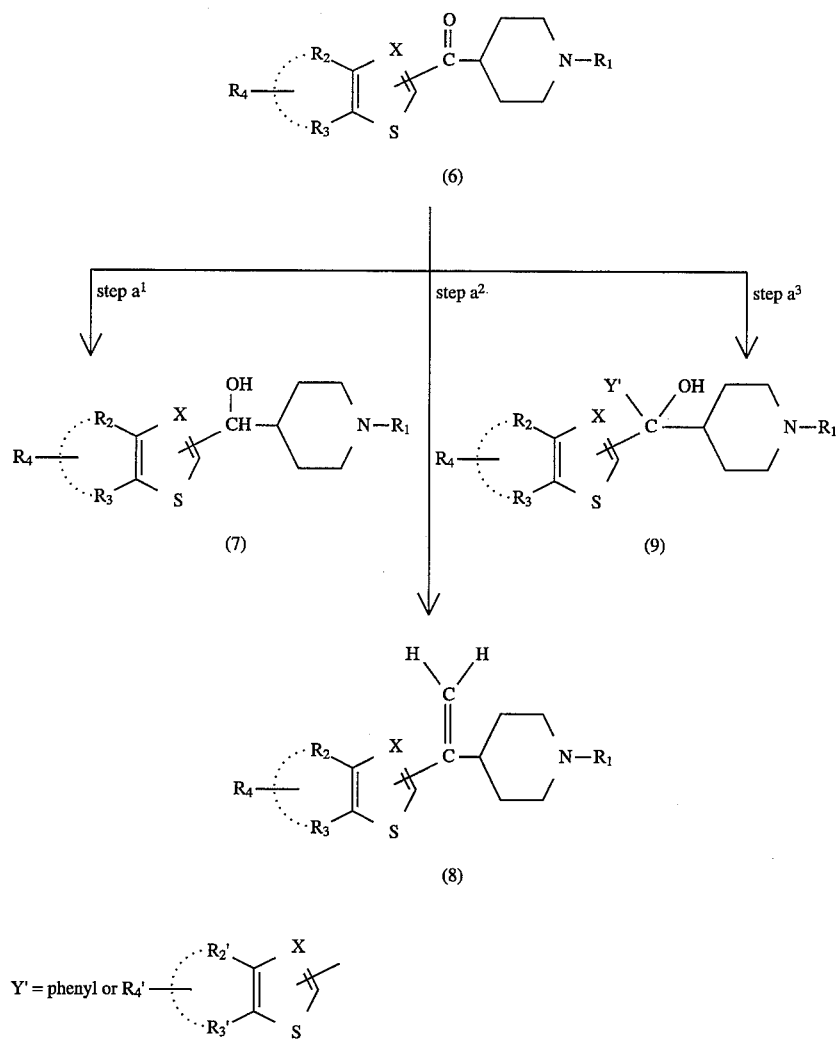

Scheme B provides a general synthetic procedure for preparing the compounds of Formula I wherein Y is —C(=CH$_2$)—, —C(H)(OH)—, —C(OH)(phenyl)— or —C(B)(OH)—.

In step a$^1$, the carbonyl functionality of the appropriate piperidinyl thiacyclic derivative of structure (6) is reduced to the corresponding hydroxymethylene group by techniques well known in the art.

For example, one suitable technique is to react the piperidinyl thiacyclic derivative of structure (6) with a reducing agent, such as sodium borohydride, in a suitable solvent such as ethanol. The piperidinyl thiacyclic derivative of structure (6) and the reducing agent are preferably present in the reaction zone in an approximately equimolar quantity. A slight excess of either reactant is not deleterious to the reaction. The reaction is allowed to proceed for a period of time ranging from about 20 minutes to about 5 hours, and more preferably about 1.5 hours. The solvent is removed under vacuum and the piperidinyl thiacyclic derivative of structure (7) can be recovered from the reaction zone by treatment with water and extraction with an organic solvent as is known in the art. The piperidinyl thiacyclic derivative of structure (7) can be purified by techniques known in the art such as recrystallization or chromatography as described previously in Scheme A, step a.

In step a$^2$, the carbonyl functionality of the appropriate piperidinyl thiacyclic derivative of structure (6) is converted to the corresponding ethenylene group by techniques well known in the art.

For example, one suitable technique is to react the piperidinyl thiacyclic derivative of structure (6) with a suitable ylide such as triphenylphosphonium methylide, in a suitable solvent such as tetrahydrofuran. The piperidinyl thiacyclic derivative of structure (6) and the triphenylphosphonium methylide are preferably present in the reaction zone in an approximately equimolar quantity. A slight excess of either reactant is not deleterious to the reaction. The reaction is allowed to proceed for a period of time ranging from about 20 minutes to about 5 hours, and more preferably about 2 hours; at a temperature range of from about −40° C. to room temperature, and more preferably about −10° C. The reaction is then quenched with a proton source such as, for example, water or saturated aqueous ammonium chloride. The resulting reaction mixture is extracted with a suitable solvent, such as ethyl ether, dried over either Na$_2$SO$_4$ or MgSO$_4$, filtered and the solvent evaporated in vacuo. The piperidinyl thiacyclic derivative of structure (8) can be purified by techniques known in the art such as recrystallization or chromatography as described previously in Scheme A, step a.

In step a³, the carbonyl functionality of the appropriate piperidinyl thiacyclic derivative of structure (6) is converted to the corresponding phenyl tertiary alcohol or thiacyclic tertiary alcohol group by techniques well known in the art.

For example, one suitable technique is to react the piperidinyl thiacyclic derivative of structure (6) with a suitable lithio thiacyclic derivative of structure (1) or phenyllithium in a suitable solvent such as tetrahydrofuran. The piperidinyl thiacyclic derivative of structure (6) and the suitable lithio thiacyclic derivative of structure (1) or phenyllithium are preferably present in the reaction zone in an approximately equimolar quantity. A slight excess of either reactant is not deleterious to the reaction. The reaction is allowed to proceed for a period of time ranging from about 5 minutes to about 5 hours, and more preferably about 30 minutes; at a temperature range of from about −90° C. to −40° C., and more preferably about −78° C. The reaction is then quenched with a proton source such as, for example, saturated aqueous ammonium chloride or methanol. The resulting reaction mixture is extracted with a suitable solvent, such as ethyl ether, dried over either Na₂SO₄ or MgSO₄, filtered and the solvent evaporated in vacuo. The piperidinyl thiacyclic derivative of structure (9) can be purified by techniques known in the art such as recrystallization or chromatography as described previously in Scheme A, step a.

Alternatively, those piperidinyl thiacyclic derivatives of structure (7), those piperidinyl thiacyclic derivatives of structure (8) and those piperidinyl thiacyclic derivatives of structure (9) wherein $R_1$ is —$(CH_2)_n$—Z—$(CH_2)_m COR_5$ wherein $R_5$ is OH or

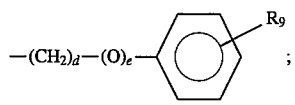

wherein $R_9$ is $CO_2R_{11}$ and $R_{11}$ is H may be prepared from the appropriate piperidinyl thiacyclic derivatives of structure (7), the piperidinyl thiacyclic derivatives of structure (8) and the piperidinyl thiacyclic derivatives of structure (9) wherein $R_1$ is —$(CH_2)_n$—Z—$(CH_2)_m COR_5$ wherein $R_5$ is $C_{1-4}$ alkoxy or

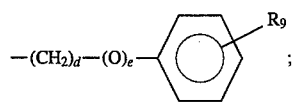

wherein $R_9$ is $CO_2R_{11}$ and $R_{11}$ is $C_{1-4}$ alkyl via an ester hydrolysis reaction as is known in the art.

Starting materials for use in Scheme B are readily available to one of ordinary skill in the art.

The following examples present typical syntheses as described in Scheme B. These examples are understood to be illustrative only and are not intended to limit the scope of the present invention in any way.

EXAMPLE 32

α-[1-[2-(4-Methoxyphenyl)ethyl]-4-piperidinyl]-α-phenyl-2-benzothiazolemethanol

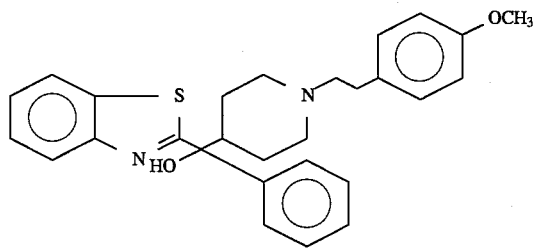

Dissolve [2-benzothiazolyl][1-[2-(4-methoxyphenyl)-ethyl]-4piperidinyl]methanone (2.0 g, 5.26 mmol) in anhydrous tetrahydrofuran (50 mL), place under an argon atmosphere and cool to −78° C. Add, by dropwise addition, phenyllithium (3.16 mL of a 2.0M solution in cyclohexane/ethyl ether, 6.31 mmol). Stir at −78° C. for 30 minutes, quench with saturated ammonium chloride (100 mL), separate the organic phase and extract the aqueous phase with ethyl acetate. Combine the organic phases, dry (MgSO₄) and evaporate the solvent in vacuo. Purify by chromatography (75% ethyl acetate/hexane) to give a yellow oil. Dissolve the oil in methylene chloride and treat with activated charcoal.

Filter and evaporate the solvent in vacuo to give the title compound as a white electrostatic powder; mp 67°–70° C.

Anal. Calcd for $C_{28}H_{30}N_2O_2S$: C, 73.33; H, 6.59; N, 6.11. Found: C, 72.73; H, 6.64; N, 5.90.

EXAMPLE 33

α-[1-[2-(4-Methoxyphenyl)ethyl]-4-piperidinyl]–2benzothiazolemethanol

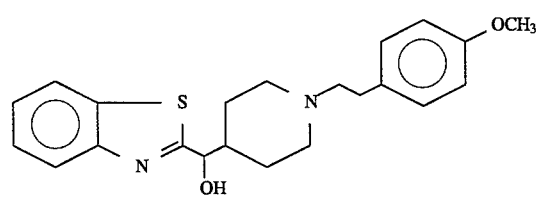

Dissolve [2-benzothiazolyl][1-[2-(4-methoxyphenyl)-ethyl]-4-piperidinyl]methanone (3.0 g, 7.88 mmol) in methanol (150 mL) and cool to 0° C. Add sodium borohydride (597 mg, 15.77 mmol) and stir for 1.5 hours, adding additional sodium borohydride after 30 minutes. Evaporate the solvent in vacuo and partition the residue between water and methylene chloride. Separate the organic phase, wash with saturated sodium chloride, dry (MgSO₄) and evaporate the solvent in vacuo. Purify by recrystallization (ethyl acetate) to give the title compound as white fluffy crystals; mp 127°–129° C.

Anal. Calcd for $C_{22}H_{26}N_2O_2S \cdot 0.25H_2O$: C, 68.27; H, 6.90; N, 7.24. Found: C, 68.30; H, 6.89; N, 7.25.

EXAMPLE 34

2-[1-[1-[2-(4-Methoxyphenyl)ethyl]-4-piperidinyl]-ethenyl]benzothiazole

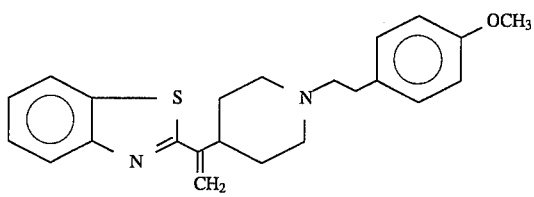

Dissolve methyltriphenylphosphonium bromide (2.50 g, 6.99 mmol) in anhydrous tetrahydrofuran (50 mL). Add n-butyllithium (2.8 mL of a 2.5M solution in hexane, 6.99 mmol) and cool to −10° C. Add, by dropwise addition, a solution of [2-benzothiazolyl][1-[2-(4-methoxyphenyl-)ethyl]-4-piperidinyl]methanone (2. 66 g, 6.99 mmol) in anhydrous tetrahydrofuran (50 mL). Stir for 2 hours then quench with water. Separate the organic phase and extract the aqueous phase with ethyl ether. Combine the organic phases, dry (MgSO$_4$) and evaporate the solvent in vacuo. Purify by chromatography (50% ethyl ether/hexane) to give the title compound as a white powder; mp 84°–85° C.

Anal. Calcd for $C_{23}H_{26}N_2OS$: C, 72.98; H, 6.92; N, 7.40. Found: C, 72.92; H, 7.01; N, 7.28.

Another general synthetic procedure for the preparation of the compounds of Formula I wherein Y is —C(=O)— or —C(H)(OH)— is set forth in Scheme C. In Scheme C, all substituents are as previously defined unless otherwise indicated.

Scheme C

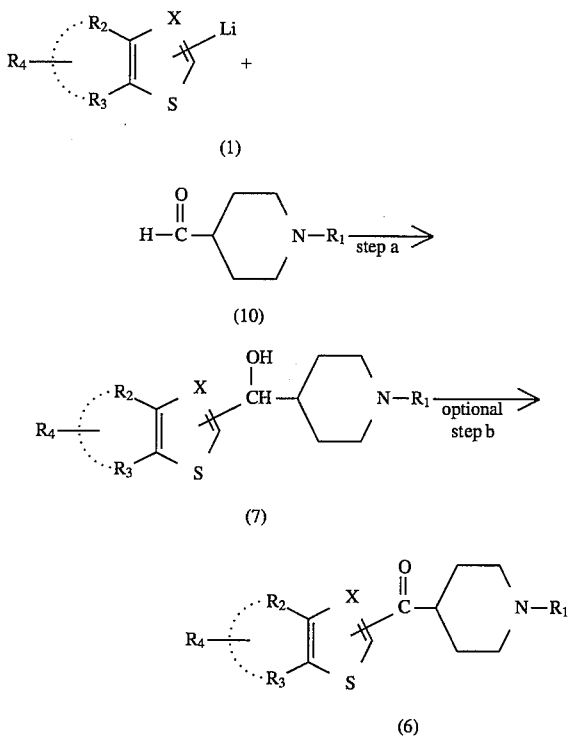

In step a, the appropriate lithio thiacyclic derivative of structure (1) is reacted with the piperidinyl derivative of structure (10) to give the corresponding piperidinyl thiacyclic derivative of structure (7).

For example, a solution of the appropriate lithio thiacyclic derivative of structure (1) is contacted with the piperidinyl derivative of structure (10) at a temperature range of from about −90° C. to about −50° C. and more preferably about −78° C. The reaction is typically conducted under anhydrous conditions in a suitable aprotic organic solvent such as tetrahydrofuran. A slight excess of either reactant is not deleterious to the reaction. The piperidinyl derivative and the benzimidazole derivative are preferably present in the reaction zone in an approximately equimolar quantity. The reaction is allowed to proceed for a period of time ranging from about 20 minutes to about 5 hours, and more preferably about 2 hours. The reaction is then quenched with a proton source such as, for example, saturated aqueous ammonium chloride or methanol. The resulting reaction mixture after dilution with water is extracted with a suitable solvent, such as ethyl acetate, washed with water, dried over either Na$_2$SO$_4$ or MgSO$_4$, filtered and the solvent evaporated in vacuo. The piperidinyl thiacyclic derivative of structure (7) can be purified by techniques known in the art such as recrystallization or chromatography as described previously in Scheme A, step a.

In optional step b, the hydroxy methylene functionality of the appropriate piperidinyl thiacyclic derivative of structure (7) is oxidized to give the corresponding piperidinyl thiacyclic derivative of structure (6) by techniques well known in the art, such as Swern Oxidation using dimethylsulfoxide, oxalyl chloride and triethylamine.

The piperidinyl thiacyclic derivatives of structure (6) may be converted to the corresponding piperidinyl thiacyclic derivatives of structures (7), (8) and (9) as described previously in Scheme B.

Starting materials for use in Scheme C are readily available to one of ordinary skill in the art. For example, 1-(2-phenylethyl)-4-piperidinecarboxyaldehyde is disclosed in U.S. Pat. No. 5,021,428 which is hereby incorporated by reference.

The following examples present typical syntheses as described in Scheme C. These examples are understood to be illustrative only and are not intended to limit the scope of the present invention in any way.

EXAMPLE 35

α-[1-(2-Phenylethyl)-4-piperidinyl]-2-benzo[b]-thiophenemethanol

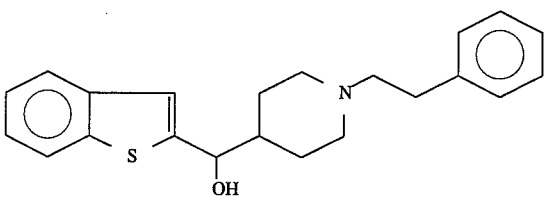

Dissolve benzo[b]thiophene (2.21 g, 16.38 mmol) in anhydrous tetrahydrofuran (70 mL), place under an argon atmosphere and cool to −78° C. Add, by dropwise addition, n-butyllithium (7.21 mL of a 2.5M solution in hexane, 18.02 mmol) and stir for 30 minutes at −78° C. Add, by dropwise addition, a solution of 1-(2-phenylethyl)-4-piperidinecarboxyaldehyde (3.56 g, 16.38 mmol) in anhydrous tetrahydrofuran (25 mL). Stir at −78° C. for 2 hours, remove the ice bath and allow to warm over 1 hour. Quench with methanol (10 mL) and pour into aqueous saturated ammonium chloride (100 mL). Separate the organic phase and extract the aqueous phase with ethyl acetate. Combine the organic phases, dry (MgSO$_4$) and evaporate the solvent in vacuo. Purify by crystallization (ethyl acetate/hexane) to give the title compound as a white crystalline solid; mp 178° C.

Anal. Calcd for C$_{22}$H$_{25}$NOS: C, 75.17; H, 7.17; N, 3.98. Found: C, 75.08; H, 7.32; N, 4.23.

EXAMPLE 36

[Benzo[b]thiophene-2-yl][1-(2-phenylethyl)-4-piperidinyl]methanone

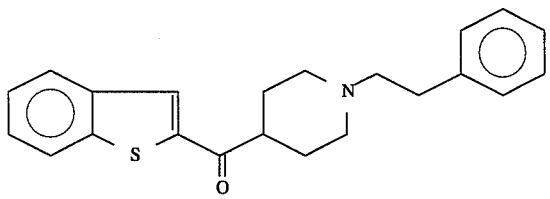

Dissolve oxalyl chloride (4.22 g, 33.28 mmol) in methylene chloride (200 mL), place under an argon atmosphere and cool to −78° C. Add, by dropwise addition, dimethylsulfoxide (5.42 g, 69.33 mmol) and stir at −78° C. for 15 minutes. Add, by dropwise addition, a solution of α-[1-(2-phenylethyl)-4-piperidinyl]-2-benzo[b]thiophenemethanol in dimethylsulfoxide (150 mL). Stir at −78° C. for 30 minutes, add triethylamine (15.18 g, 0.150 mol) and stir at −78° C. for 1 hour. Remove the ice bath and stir for an additional 1.5 hours. Evaporate the solvent in vacuo and recrystallize (isopropanol) to give the title compound as a fluffy white crystalline solid; mp 129°–130° C.

Anal. Calcd for C$_{22}$H$_{23}$NOS: C, 75.61; H, 6.63; N, 4.01. Found: C, 75.46; H, 6.63; N, 3.87.

EXAMPLE 37

α-[1-(2,Phenylethyl)-4-piperidinyl]-α-phenyl-2-benzo[b]thiophenemethanol

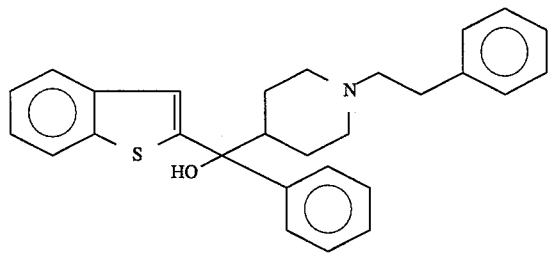

Dissolve [benzo[b]thiophene-2-yl][1-(2-phenylethyl)-4-piperidinyl]methanone (3.5 g, 10.01 mmol) in anhydrous tetrahydrofuran (100 mL), place under an argon atmosphere and cool to −78° C. Add, by dropwise addition, phenyllithium (6 mL of a 2.0M solution in cyclohexane/ethyl ether, 12.0 mmol) and stir at −78° C. for 5 hours. Remove the ice bath and allow to warm to room temperature. Pour into saturated ammonium chloride (100 mL) and stir for 20 minutes. Separate the organic phase and extract the aqueous phase with ethyl acetate. Combine the organic phases, wash with water, dry (MgSO$_4$) and evaporate the solvent in vacuo. Purify by chromatography (50% ethyl acetate/hexane) and recrystallize (isopropanol) to give the title compound as a white solid; mp 144°–146° C.

Anal. Calcd for C$_{28}$H$_{29}$NOS: C, 78.65; H, 6.84; N, 3.28. Found: C, 78.55; H, 6.94; N, 3.20.

EXAMPLE 38

α-[1-(2-Phenylethyl)-4-piperidinyl]-3benzo[b]-thiophenemethanol

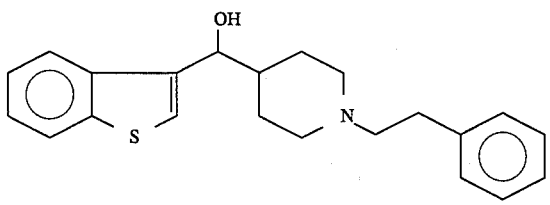

Dissolve n-butyllithium (9.4 mL of a 2.5M solution in hexane, 23.46 mmol) in anhydrous ethyl ether (100 mL), place under an argon atmosphere and cool to −78° C. Add, by dropwise addition, a solution of 3-bromobenzo[b]thiophene (5.0 g, 23.46 mmol) in anhydrous ethyl ether (50 mL). Stir at −78° C. for 30 minutes then add, by dropwise addition, a solution of 1-(2-phenylethyl)-4-piperidinecarboxaldehyde (5.10 g, 23.46 mmol) in anhydrous ethyl ether (50 mL). Stir for 5 hours at −78° C., remove the ice bath and stir for an additional 1 hour. Quench with saturated ammonium chloride (150 mL) and stir overnight. Separate the organic phase and extract the aqueous phase with ethyl ether and methylene chloride. Combine the organic phases, dry (MgSO$_4$) and evaporate the solvent in vacuo. Purify by recrystallization (isopropanol) to give the title compound as an off-white solid.

Anal. Calcd for C$_{22}$H$_{25}$NOS: C, 75.17; H, 7.17; N, 3.98. Found: C, 75.10; H, 7.22; N, 4.16.

EXAMPLE 39

[Benzo[b]thiophene-3-yl][1-(2,phenylethyl)-4-piperidinyl]methanone

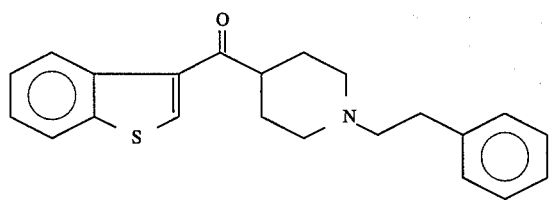

Dissolve oxalyl chloride (4.22 g, 33.28 mmol) in methylene chloride (200 mL), place under an argon atmosphere and cool to −78° C. Add, by dropwise addition, dimethylsulfoxide (5.42 g, 69.33 mmol) and stir at −78° C. for 15 minutes. Add, by dropwise addition, a solution of α-[1-(2-phenylethyl)-4-piperidinyl]-3-benzo[b]thiophenemethanol (9.75 g, 27.73 mmol) in dimethylsulfoxide (150 mL). Stir at −78° C. for 30 minutes, add triethylamine (15.18 g, 0.150 mol) and stir at −78° C. for 1 hour. Remove the ice bath and stir for an additional 1.5 hours. Evaporate the solvent in vacuo and recrystallize (isopropanol) to give the title compound as a tan powder; mp 110°–112° C.

Anal. Calcd for C$_{22}$H$_{23}$NOS: C, 75.61; H, 6.63; N, 4.01. Found: C, 75.66; H, 6.74; N, 3.98.

EXAMPLE 40

α-[1-(2-Phenylethyl)-4-piperidinyl]-2-thiophenemethanol

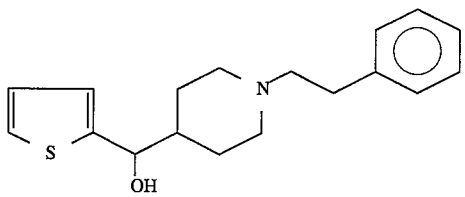

Dissolve 1-(2-phenylethyl)-4-piperidinecarboxaldehyde (10.0 g, 46.02 mmol) in anhydrous tetrahydrofuran (300 mL), place under an argon atmosphere and cool to −78° C. Add, by dropwise addition, a solution of 2-lithiothiophene (46.02 mL of a 1M solution in tetrahydrofuran, 46.02 mmol) and stir for 3 hours at −78° C. Quench with saturated ammonium chloride, separate the organic phase and extract the aqueous phase with ethyl acetate. Combine the organic phases, dry (MgSO$_4$) and evaporate the solvent in vacuo. Purify by chromatography (ethyl acetate) and recrystallize (cyclohexane) to give the title compound as a white solid; mp 123°–125° C.

Anal. Calcd for $C_{18}H_{23}NOS$: C, 71.72; H, 7.69; N, 4.65. Found: C, 71.76; H, 7.88; N, 4.57.

EXAMPLE 41

[Thiophene-2-yl][1-(2-phenylethyl)-4-piperidinyl]-methanone

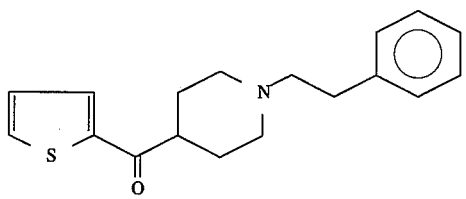

Dissolve oxalyl chloride (1.23 g, 9.67 mmol) in methylene chloride (100 mL), place under an argon atmosphere and cool to −78° C. Add dimethylsulfoxide (1.43 mL) and stir for 15 minutes. Add, by dropwise addition, a solution of α-[1-(2-phenylethyl)-4-piperidinyl]–2-thiophenemethanol 8.06 mmol) in methylene chloride (100 mL). Stir at −78° C. for 30 minutes, then add triethylamine (6.07 mL). Stir at −78° C. for 30 minutes, remove the ice bath and allow to warm to room temperature. Evaporate the solvent in vacuo and partition between methylene chloride and water. Separate the organic phase and extract the aqueous phase with methylene chloride. Combine the organic phases, wash with water and dry (MgSO$_4$). Evaporate the solvent in vacuo and recrystallize (isopropanol) to give the title compound as a white crystalline solid; mp 77°–79° C.

Anal. Calcd for $C_{18}H_{21}NOS$: C, 72.20; H, 7.07; N, 4.68. Found: C, 72.13; H, 7.18; N, 4.61.

EXAMPLE 42

α-[1-(2phenylethyl)-4-piperidinyl]-2-thiazolemethanol

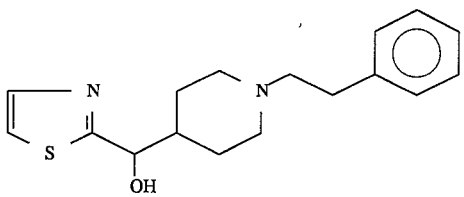

Prepare according to the procedure described in Example 29 using 2-lithiothiazole.

EXAMPLE 43

[2-Thiazolyl][1-(2,phenylethyl)-4-piperidinyl]-methanone

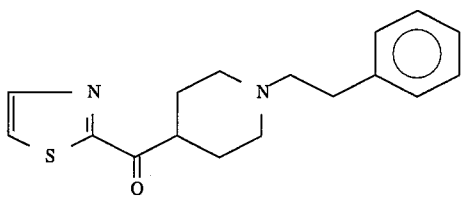

Prepare according to the procedure described in Example 30 using α-[1-(2-phenylethyl)-4-piperidinyl]-2-thiazolemethanol.

Another general synthetic procedure for the preparation of the compounds of Formula I wherein Y is —C(=O)— is set forth in Scheme D. In Scheme D, all substituents are as previously defined unless otherwise indicated.

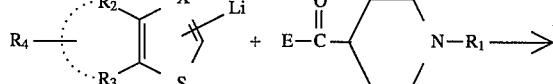

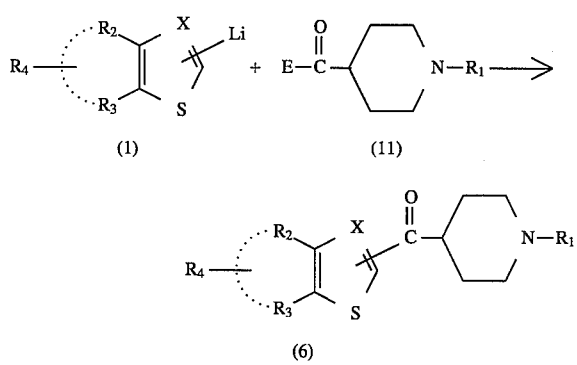

E=$C_1$–$C_4$ alkoxy or N(OCH$_3$)CH$_3$

Scheme D provides a general synthetic procedure for preparing the compounds of Formula (I) wherein Y is —C(=O)—.

For example, a solution of the appropriate lithio thiacyclic derivative of structure (1) is contacted with the piperidinyl derivative of structure (11) at a temperature range of from about −90° C. to about −50° C. and more preferably about −78° C. The reaction is typically conducted under anhydrous conditions in a suitable aprotic organic solvent such as tetrahydrofuran. A slight excess of either reactant is not deleterious to the reaction. The piperidinyl derivative and the benzimidazole derivative are preferably present in the reaction zone in an approximately equimolar quantity. The reaction is allowed to proceed for a period of time ranging from about 20 minutes to about 5 hours, and more preferably about 1 hour. The reaction is then quenched with a proton source such as, for example, saturated aqueous ammonium chloride or methanol. The resulting reaction mixture is extracted with a suitable solvent, such as ethyl acetate, washed with water, dried over either $Na_2SO_4$ or $MgSO_4$, filtered and the solvent evaporated in vacuo. The piperidinyl thiacyclic derivative of structure (6) can be purified by techniques known in the art such as recrystallization or chromatography as described previously in Scheme A, step a.

The piperidinyl thiacyclic derivatives of structure (6) may be converted to the corresponding piperidinyl thiacyclic derivatives of structures (7), (8) and (9) as described previously in Scheme B.

Starting materials for use in Scheme D are readily available to one of ordinary skill in the art. For example, 1-[2-(4-methoxyphenyl)ethyl]-4-piperidinecarboxylic acid, methyl ester is described in *J. Org. Chem.*, 55, 1399 1990.

The following example presents a typical synthesis as described in Scheme D. This example is understood to be illustrative only and is not intended to limit the scope of the present invention in any way.

EXAMPLE 44

[2Benzothiazolyl][1-[2-(4-methoxyphenyl)ethyl]-4-piperidinyl]methanone

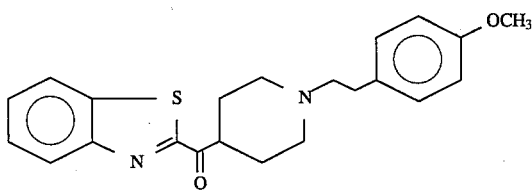

Dissolve freshly distilled benzothiazole (3.41 g, 25.24 mmol) in anhydrous tetrahydrofuran (60 mL), place under an argon atmosphere and cool to −78° C. Add, by dropwise addition, n-butyllithium (15.14 mL of a 2.5M solution in hexane, 37.86 mmol) and stir briefly at −78° C. Add, by dropwise addition, a solution of 1-[2-(4-methoxyphenyl)-ethyl]-4-piperidinecarboxylic acid, methyl ester (7.0 g, 25.24 mmol) in anhydrous tetrahydrofuran (40 mL). Stir for 1 hour at −78° C., quench with methanol (5 mL) and pour into saturated ammonium chloride (100 mL). Filter, separate the organic phase and extract the aqueous phase with ethyl acetate. Combine the organic phases and wash with water and brine. Dry ($MgSO_4$) and evaporate the solvent in vacuo. Purify by chromatography (ethyl acetate) and recrystallize (cyclohexane) to give the title compound as a pale yellow powder; mp 118°–120° C.

Anal. Calcd for $C_{22}H_{24}N_2O_2S$: C, 69.44; H, 6.36; N, 7.36. Found: C, 69.65; H, 6.51; N, 7.21.

EXAMPLE 10 gives an alternative method of making this compound.

A general synthetic procedure for the preparation of the compounds of Formula I wherein Y is —C(B)(OH)— wherein B and the thiacyclic portion of the compound of Formula I are identical is set forth in Scheme E. In Scheme E, all substituents are as previously defined unless otherwise indicated.

Scheme E

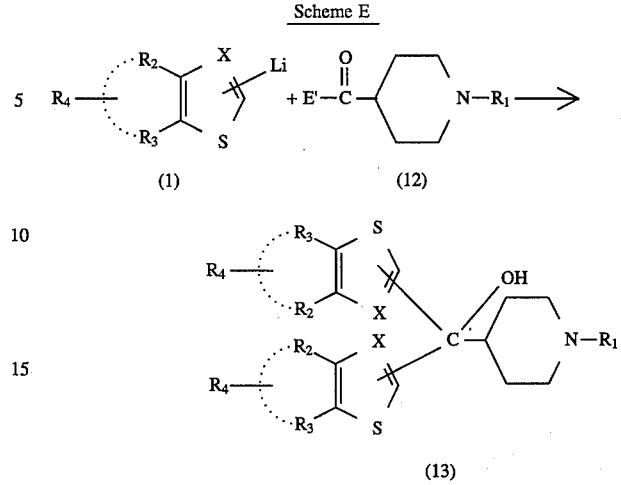

$E'=C_1-C_4$ alkoxy

The appropriate lithio thiacyclic derivative of structure (1) is reacted with the piperidinyl derivative of structure (12) to give the corresponding bis(thiacyclic) tertiary alcohol derivative of structure (13).

For example, a solution of the appropriate lithio thiacyclic derivative of structure (1) is contacted with the piperidinyl derivative of structure (12) at a temperature range of from about −90° C. to about −50° C. and more preferably about −78° C. The reaction is typically conducted under anhydrous conditions in a suitable aprotic organic solvent such as tetrahydrofuran. The piperidinyl derivative and the lithio thiacyclic derivative are preferably present in the reaction zone in an approximately a 1:2 ratio. The reaction is allowed to proceed for a period of time ranging from about 20 minutes to about 5 hours, and more preferably about 2 hours. The reaction is then quenched with a proton source such as, for example, saturated aqueous ammonium chloride or methanol. The resulting reaction mixture is extracted with a suitable solvent, such as ethyl acetate, washed with water, dried over either $Na_2SO_4$ or $MgSO_4$, filtered and the solvent evaporated in vacuo. The bis(thiacyclic) tertiary alcohol derivative of structure (13) can be purified by techniques known in the art such as recrystallization or chromatography as described previously in Scheme A, step a.

Alternatively, those bis(thiacyclic) tertiary alcohol derivatives of structure (13) wherein $R_1$ is —$(CH_2)_n$—Z—$(CH_2)_m COR_5$ wherein $R_5$ is OH or

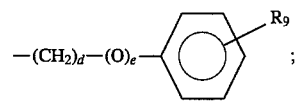

wherein $R_9$ is $CO_2R_{11}$ and $R_{11}$ is H may be prepared from the appropriate bis(thiacyclic) tertiary alcohol derivatives of structure (13) wherein $R_1$ is —$(CH_2)_n$—Z—$(CH2)_m COR_5$ wherein $R_5$ is $C_{1-4}$ alkoxy or

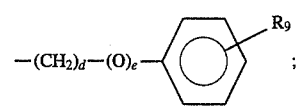

wherein $R_9$ is $CO_2R_{11}$ and $R_{11}$ is $C_{1-4}$ alkyl via an ester hydrolysis reaction as is known in the art.

Starting materials for use in Scheme E are readily available to one of ordinary skill in the art.

The following examples present typical syntheses as described in Scheme E. These examples are understood to be illustrative only and are not intended to limit the scope of the present invention in any way.

EXAMPLE 45

α-[1-[2-(4-Methoxyphenyl)ethyl]-4-piperidinyl]-
α(thiophene-2-yl)-2-thiophenemethanol

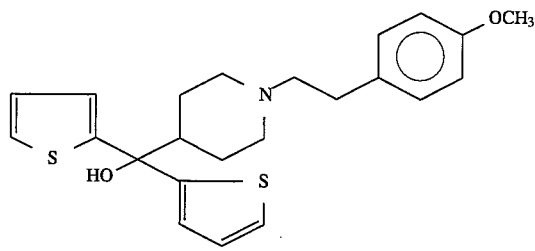

Dissolve 1-[2-(4-methoxyphenyl)ethyl]-4-piperidinecarboxylic acid, methyl ester (4.0 g, 14.42 mmol) in anhydrous tetrahydrofuran (100 mL), place under an argon atmosphere and cool to −78° C. Add, by dropwise addition, 2-lithiothiophene (14.42 mL of a 1M solution in tetrahydrofuran, 14.42 mmol) and stir at −78° C. for 3 hours. Add additional 2-lithiothiophene (14.42 mL of a 1M solution in tetrahydrofuran, 14.42 mmol) and stir at −78°C. for 2 hours. Remove the ice bath and allow to warm to room temperature. Quench with saturated ammonium chloride (100 mL), separate the organic phase and extract the aqueous phase with ethyl acetate. Combine the organic phases, dry (MgSO$_4$) and evaporate the solvent in vacuo. Purify by chromatography (ethyl acetate) and recrystallize (ethyl acetate) to give the title compound as fluffy white crystals; mp 153°–155° C.

Anal. Calcd for $C_{23}H_{27}NO_2S_2$: C, 66.79; H, 6.58; N, 3.39. Found: C, 66.68; H, 6.40; N, 3.49.

EXAMPLE 46

α-[1-[2-(4-Methoxyphenyl)ethyl]-4-piperidinyl]-
(2thiazolyl)-2-thiazolemethanol

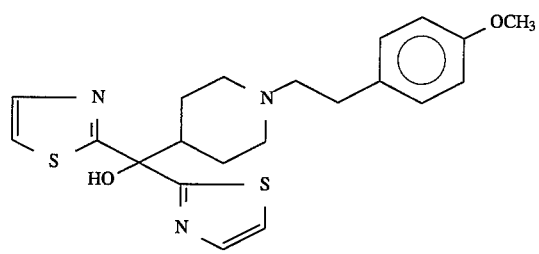

Prepare according to the procedure described in Example 34 using 2-lithiothiazole.

EXAMPLE 47

α-[1-[2-(4-Methoxyphenyl)ethyl]-4-piperidinyl]-
α-(benzo[b]thiophene-2-yl)-2-
benzo[b]thiophenemethanol

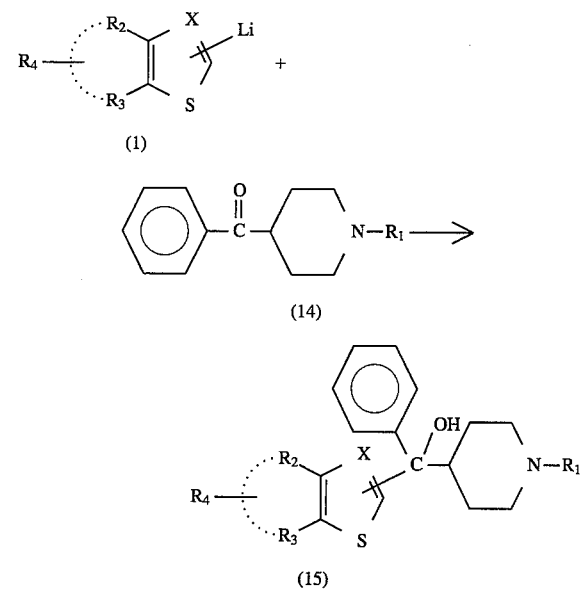

Dissolve benzo[b]thiophene(10.0 g, 74.5 mmol) in anhydrous tetrahydrofuran (100 mL), place under an argon atmosphere and cool to −78° C. Add, by dropwise addition, n-butyllithium (32.79 mL, 81.97 mmol) and stir briefly. Add, by dropwise addition, a solution of 1-[2-(4-methoxyphenyl)-ethyl]-4-piperidinecarboxylic acid, methyl ester (20.67 g, 74.52 mmol) in anhydrous tetrahydrofuran (200 mL) and stir at −78° C. for 1.5 hours. Quench with saturated ammonium chloride, separate the organic phase and extract the aqueous phase with ethyl ether. Combine the organic phases, dry (MgSO$_4$) and evaporate the solvent in vacuo. Purify by chromatography (50% ethyl acetate/hexane) and recrystallize (isopropanol) to give the title compound as a white solid; mp 168°–179° C.

Anal. Calcd for $C_{23}H_{25}NO_2S$: C, 72.79; H, 6.64; N, 3.69. Found: C, 72.34; H, 6.15; N, 2.63.

Another general synthetic procedure for the preparation of the compounds of Formula I wherein Y is —C(OH)(phenyl)— is set forth in Scheme F. In Scheme F, all substituents are as previously defined unless otherwise indicated.

For example, a solution of the appropriate lithio thiacyclic derivative of structure (1) is contacted with the piperidinyl derivative of structure (14) at a temperature range of from about −90° C. to about −50° C. and more preferably about −78° C. The reaction is typically conducted under anhydrous conditions in a suitable aprotic organic solvent such as tetrahydrofuran. The piperidinyl derivative and the lithio thiacyclic derivative are preferably present in the reaction zone in an approximately equimolar quantity. A slight excess of either reactant is not deleterious to the reaction. The reaction is allowed to proceed for a period of time ranging from about 20 minutes to about 5 hours, and more preferably about 2 hours. The reaction is then quenched with a proton source such as, for example, saturated aqueous ammonium chloride or methanol. The resulting reaction mixture is extracted with a suitable solvent, such as ethyl acetate, washed with water, dried over either $Na_2SO_4$ or $MgSO_4$, filtered and the solvent evaporated in vacuo. The piperidinyl thiacyclic derivative of structure (15) can be purified by techniques known in the art such as recrystallization or chromatography as described previously in Scheme A, step a.

Alternatively, those piperidinyl thiacyclic derivatives of structure (15) wherein $R_1$ is —$(CH_2)_n$—Z—$(CH_2)_m COR_5$ wherein $R_5$ is OH or

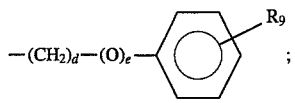

wherein $R_9$ is $CO_2R_{11}$ and $R_{11}$ is H may be prepared from the appropriate piperidinyl thiacyclic derivatives of structure (15) wherein $R_1$ is —$(CH_2)_n$—Z—$(CH_2)_m COR_5$ wherein $R_5$ is $C_{1-4}$ alkoxy or

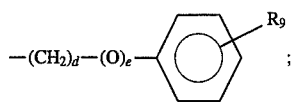

wherein $R_9$ is $CO_2R_{11}$ and $R_{11}$ is $C_{1-4}$ alkyl via an ester hydrolysis reaction as is known in the art.

Starting materials for use in Scheme F are readily available to one or ordinary skill in the art. For example, phenyl[1-(2-phenylethyl)-4-piperidinyl]methanone.HCl and α-[1-(2-phenylethyl)- 4-piperidinyl]phenylmethanol.HCl is disclosed in U.S. Pat. No. 5,021,428 which is hereby incorporated by reference.

The following example presents a typical synthesis as described in Scheme F. This example is understood to be illustrative only and is not intended to limit the scope of the present invention in any way.

EXAMPLE 48

α-[1-(2-Phenylethyl)-4-piperidinyl]-α-phenyl-2thiophenemethanol

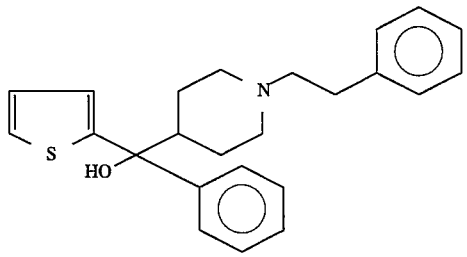

Mix phenyl[1-(2-phenylethyl)-4-piperidinyl]methanone-.HCl (5.0 g, 15.16 mmol), 1N sodium hydroxide (100 mL) and methylene chloride (250 mL) and stir overnight at room temperature. Separate the organic phase and extract the aqueous phase with methylene chloride. Combine the organic phases, dry ($MgSO_4$) and evaporate the solvent in vacuo to give phenyl[1-(2-phenylethyl)-4-piperidinyl]methanone.

Dissolve phenyl[1-(2-phenylethyl)-4-piperidinyl]methanone (4.45 g, 15.16 mmol) in anhydrous tetrahydrofuran (40 mL), place under an argon atmosphere and cool to −78° C. Add, by dropwise addition, 2-lithiothiophene (15.16 mL of a 1M solution in tetrahydrofuran, 15.16 mmol) and stir at −78° C. for 1.5 hours. Quench with saturated ammonium chloride, separate the organic phase and extract the aqueous phase with ethyl ether. Combine the organic phases, dry ($MgSO_4$) and evaporate the solvent in vacuo. Purify by chromatography (50% ethyl acetate/hexane) and recrystallize (cyclohexane) to give the title compound as a white crystalline solid; mp 143°–144° C.

Anal. Calcd for $C_{24}H_{27}NOS$: C, 76.35; H, 7.21; N, 3.71. Found: C, 76.34; H, 7.32; N, 3.59.

EXAMPLE 49

α-[1-(2-Phenylethyl)-4-piperidinyl]-α-phenyl-2-thiazolemethanol

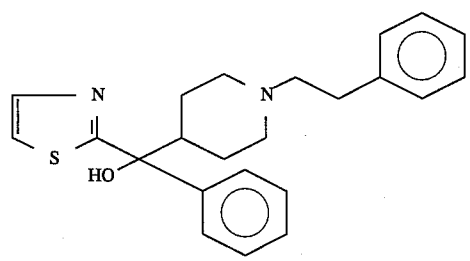

Prepare according to the procedure described in Example 37 using 2-lithiothiazole.

The compounds of the present invention are useful as non-sedating $H_1$ anti-histamines and mediator release inhibitors and are thus useful in the treatment of a variety of allergic diseases such as allergic rhinitis, seasonal rhinitis, allergic dermatoses such as acute urticaria, atopic dermatitis, contact dermatitis, gastrointestinal allergies which can be caused by the ingestion of either food or drugs, allergic pulmonary disease, ophthalmic allergies, insect stings and anaphylaxis, including the inhibition of brochospasms. These conditions and diseases can be relieved by administering to the patient in need thereof the compounds of formula I in an amount sufficient to treat the disease or condition such as an anti-allergic disease amount.

Since compounds of formula I are also seratonin $5HT_2$ antagonists, they are useful in the treatment of a variety of disease states and conditions such as the treatment of anxiety, variant angina, anorexia nervosa, Raynaud's phenomenon, intermittent claudication and coronary or peripheral vasospasms. Also, these compounds can be used to treat late restenosis and to inhibit the development of atherosclerosis. The compounds inhibit the development of vascular smooth muscle cell hyperplasia. They should be administered on a prophylactic basis to prevent the development of this condition. These conditions and diseases can be relieved by administering to the patient in need thereof the compounds of formula I in an amount sufficient to treat the disease or condition such as an anxiolytic amount, antianginal amount, anti-anorexic amount. This can also be defined as an amount effective in treating a patient having a disease which responds to antagonism of $5HT_2$ receptors. This quantity will be within the dosage range at which the compound exhibits its serotonin $5HT_2$ antagonistic properties.

One method of demonstrating the utility of the compounds of Formula I as anti-allergic disease agents is the following test protocol. One group of 10 guinea pigs is dosed orally with from about 0.1 mg/kg to about 100 mg/kg of the test compound. A control group of 10 guinea pigs is dosed orally with a similar volume of a vehicle (a solution of 0.5% methylcellulose and 1% ethanol). Both groups should be anesthetized and their dorsal areas shaved. One hour later, both groups are given intravenous injections of 1% Evans Blue Dye (1ml) via the jugular vein. Immediately following the dye injection, both groups are injected intradermally in the dorsal area with histamine diphosphate injections (1μg/0.1 ml) to produce histamine wheals. Twenty minutes after injection of the histamine, the animals are sacrificed and the size of the wheal area is then calculated from the diameter of the exposed wheal. A compound is considered to possess antihistamine activity if the wheal area of the drug treated group is statistically smaller than that of the control group.

Any other method for testing the compounds of Formula I for anti-allergic efficacy may be used. For example, see Van Rossum, J. M., *Arch, Int. Pharmacodyn.* 143:299 (1963); Chang, R. S. L, et al. and Histamine $H_1$Receptors in Brain Labeled with [$^3$H]Mepyramine., *Eur. J. Pharmacol.* 48:463–464 (1978). Mediator release inhibition may be tested according to published methods, one of which is Yanagihara, Y., Abe, T., Kuroda, T. and Shida, T., Immunopharmacological actions of the new antiallergic drug butyl 3'-(1H-trtrazol-5-yl)oxamilate. *Arzneim.-Forsch.* 38:80–83 (1988).

Likewise, the compounds of Formula I can be tested by any appropriate method for $5HT_2$ antagonism. The ability of the compounds to antagonize the effects of serotonin at the $5HT_2$ receptor can be demonstrated by the spiroperidol binding test as described by Peroutka et al., in *Mol. Pharmacol.*, Vol. 16, pages 687–699 (1979). In this test, $5HT_2$ receptors are exposed to both [$^3$H] spiroperidol, (a substance known to have a specific affinity for the receptor) and the test compound. The extent to which there is a decrease in binding of the [$^3$H] spiroperidol to the receptor is indicative of the affinity of the test compound for the $5 HT_2$ receptor.

The ability of the compounds to antagonize the $5 HT_2$ receptors in vivo the brain can be demonstrated via the 5-DMT head twitch test as described by Friedman et al. in *Commun. Psychopharmocal*, Vol. 3, pages 89–92, (1979). The administration of 5-methoxy-N,N-dimethyltryptamine (DMT) to mice typically produces a characteristic head twitch in the mice. In this test, the mice are administered 5-DMT and a test compound. An absence of head twitches in the mice is considered to be predictive of the ability of the test compound to antagonize the $5 HT_2$ receptor in vivo.

An anti-allergic disease amount of the compounds of Formula I will vary with the disease being treated, the severity of the disease, the condition of the patient, the route of administration and a number of other conditions well known to those skilled in the art. Typically, an anti-allergic amount of the compounds of Formula I is about 0.01 mg/kg/day to about 120 mg/kg/day. This dose may be divided into a number of doses per day depending upon the result desired. This is also the dose for use separately as an antihistamine and the dose for use separately as a mediator release inhibitor.

Likewise, the dosage range at which these compounds exhibit their ability to block the effects of serotonin at the $5 HT_2$ receptor can vary depending upon the particular compound being administered, the particular disease or condition being treated and its severity, the patient, other underlying disease states the patient is suffering from, and other medications that may be concurrently administered to the patient. Generally though, these compounds will exhibit their serotonin $5 HT_2$ antagonist properties at a dosage range of from about 0.001 mg/kg of patient body weight/day to about 4.0 mg/kg of patient body weight/day. The compounds can be administered orally or parenterally to achieve these effects.

"Treatment" means the ability of the compound to reduce the severity of or alleviate the symptoms related to the disease or be used prophylactically.

The compounds of the present invention are administered to a patient in need of such therapy. "Patient" means a mammal such as a guinea pig or other rodent, dog, cat, or human. The route of administration may be by any appropriate method known to those skilled in the art such as oral, buccal, sublingual, parenteral, topical, opthalmical or by inhalation.

Pharmaceutical compositions can be manufactured utilizing techniques known in the art. Typically an effective amount of the compound to treat a specified disease will be admixed with a pharmaceutically acceptable carrier.

For oral administration, the compounds can be formulated into solid or liquid preparation such as capsules, tablets, lozenges, powders, suspensions or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents and preservative agents as are known in the art.

For parenteral administration the compounds may be dissolved in a physiologically acceptable carrier and administered as either a solution or a suspension. Illustrative of suitable pharmaceutical carriers are water, saline, dextrose solutions, fructose solutions, ethanol or oils of animal, vegetable or synthetic original. The pharmaceutical carrier may also contain preservatives, buffers, etc., as are known in the art.

For nasal administration, the compounds may be dissolved in a physiologically acceptable pharmaceutical carrier and administered as a solution. Illustrative of suitable pharmaceutical carriers are water, saline, and aqueous alcoholic solutions. The pharmaceutical carrier may also contain preservatives, buffers, etc., as are known in the art.

For topical administration, the compounds can be incorporated into a suitable topical carrier using techniques well known in the art. Examples of suitable topical carriers include oleaginous bases such as white petrolatum, absorption bases such as hydrophilic petrolatum, emulsion bases such as lanolin, and water soluble bases such as polyethylene glycol ointment. The topical carrier may also contain preservatives, buffers, etc., as are known in the art.

For inhalation therapy, the compounds can be incorporated into an aqueous alcoholic solution containing a fluorinated hydrocarbon propellant and packaged into a suitable administration device as known in the art.

What is claimed is:

1. A compound of the formula:

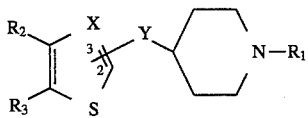

optical isomers or pharmaceutically acceptable salts thereof, wherein

Y is —C(H)(OH)—, wherein Y is attached at the heterocycle position 2 or 3;

X is carbon, CH or nitrogen, provided that when Y is attached at the 3 position X is carbon, and when Y is attached at the 2 position X is CH or nitrogen;

$R_1$ is —$(CH_2)_n$—Z—$(CH_2)_m COR_5$, —$C(O)R_8$ or

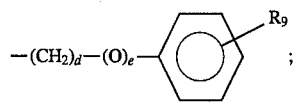

$R_2$ and $R_3$ are the same or different and are hydrogen or $C_{1-4}$ alkyl;

Z is a bond, O, or S;

$R_5$ is OH, $C_{1-4}$ alkoxy or —$NR_6R_7$;

$R_6$ and $R_7$ are same or different and are H or $C_{1-4}$ alkyl;

$R_8$ is $C_{1-4}$ alkyl, $C_{1-4}$ alkoxy;

$R_9$ is H, $C_{1-4}$ alkyl, $C_{1-4}$ alkoxy, OH, chloro, bromo, fluoro, —$CF_3$, —$NHC(O)R_{10}$, or $CO_2R_{11}$;

$R_{10}$ is $C_{1-4}$ alkyl or $C_{1-4}$ alkoxy;

$R_{11}$ is hydrogen or $C_{1-4}$ alkyl;

n is an integer from 0–3 provided that when Z is not a bond, n is an integer from 2–3;

m is an integer from 1 to 3;

d is an integer from 1–5; and e is zero or 1, provided that when e is 1:
    d is an integer from 2 to 5.

2. The compound of claim 1 wherein X is nitrogen.

3. The compound of claim 1 wherein $R_1$ is

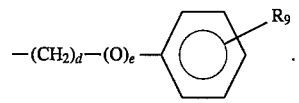

4. The compound of claim 3 wherein d is 2, e is 0 and $R_9$ is $CO_2R_{11}$.

5. The compound of claim 1 wherein X is CH or carbon.

6. A compound of claim 1 which is α-[1-(2-Phenylethyl)-4-piperidinyl]-2-thiophenemethanol.

7. A compound of claim 1 which is α-[1-(2-Phenylethyl)-4-piperidinyl]-2-thiazolemethanol.

8. A pharmaceutical composition comprising the compound of claim 1 and a pharmaceutically acceptable carrier.

9. A method of treating a patient having an allergic disease with an effective amount of the compound of claim 1.

* * * * *

UNITED STATES PATENT AND TRADEMARK OFFICE
CERTIFICATE OF CORRECTION

PATENT NO. : 5,602,147
DATED : Feb. 11, 1997
INVENTOR(S) : Albert A. Carr, et al.

It is certified that error appears in the above-identified patent and that said Letters Patent is hereby corrected as shown below:

At column 1, line 19, the patent reads "5HT2" and should read --5HT$_2$--.
At column 9, line 15, the patent reads "1,1dimethylethyl" and should read --1,1-dimethylethyl--.
At column 10, line 38, the patent reads "in in vacuo" and should read --in vacuo--.
At column 11, line 5, the patent reads "-4piperidinyl" and should read -- -4-piperidinyl --.
At column 13, line 4, the patent reads "-1piperidinyl" and should read -- -1-piperidinyl --.
At column 13, line 18, the patent reads "(3iodopropoxy)" and should read --(3-iodopropoxy)--.
At column 14, line 42, the patent reads "(5chloropentoxy)" and should read --(5-chloropentoxy)--.
At column 16, line 44, the patent reads "-dimethylthyl" and should read -- -dimethylethyl --.
At column 17, line 7, the patent reads "1,1dimethylethyl" and should read -- 1,1-dimethylethyl --.
At column 17, line 58, the patent reads "(4methoxyphenyl" and should read
-- (4-methoxyphenyl --.

Col. 18, line 35, "amino]carbonyl]-1-carbonyl]-1-piperidine" should read --amino]carbonyl]-1-piperidine --.

At column 20, line 22, the patent reads "6fluoro" and should read -- 6-fluoro --.
At column 21, line 10, the patent reads "methanonee.CF$_3$CO$_2$H" and should read
-- methanone•CF$_3$CO$_2$H --.
At column 22, line 57 the patent reads "methyl" and should read --methyl ester--.
At column 26, line 19, the patent reads "-4piperidinyl]" and should read -- -4-piperidinyl] -- .
At column 26, line 34, the patent reads "C$_{28H30}$" and should read --C$_{28}$H$_{30}$ --.
At column 26, line 43, the patent reads "2benzothiazolemethanol" and should read
-- 2-benzothiazolemethanol --.
At column 29, line 56, the patent reads "(2-phenylethyl)" and should read -- (2-phenylethyl)--
At column 31, line 54, the patent reads "8.06 mmol) and should read -- (2.43 g, 8.06 mmol) --.

UNITED STATES PATENT AND TRADEMARK OFFICE
CERTIFICATE OF CORRECTION

PATENT NO. : 5,602,147
DATED : Feb. 11, 1997
INVENTOR(S) : Albert A. Carr, et al.

It is certified that error appears in the above-identified patent and that said Letters Patent is hereby corrected as shown below:

At column 32, line 3 and 19 the patent reads "(2phenylethyl)" and should read -- (2-phenylethyl)--
At column 33, line 30, the patent reads "[2Benzothiazolyl]" and should read
--[2-Benzothiazolyl]--

At column 35, line 12, the patent reads "-α(thiophene" and should read -- -α-(thiophene --.
At column 35, line 52, the patent reads "-(2thiazolyl)" and should read -- -α(thiazolyl1)—
At column 38, line 4, the patent reads "-2thiophenemethanol" and should read
-- -2-thiophenemethanol--.
At column 42, line 12 in claim 1, the patent reads "are same" and should read --are the same--.

Signed and Sealed this

Sixth Day of October, 1998

Attest:

BRUCE LEHMAN

*Attesting Officer*   *Commissioner of Patents and Trademarks*